(12) United States Patent
Bolduc et al.

(10) Patent No.: US 8,461,129 B2
(45) Date of Patent: Jun. 11, 2013

(54) SUPERABSORBENT SURFACE-TREATED CARBOXYALKYLATED POLYSACCHARIDES AND PROCESS FOR PRODUCING SAME

(75) Inventors: Isabelle Bolduc, Chambly (CA); Anne-Claude Couffin, Monestier de Clermont (FR); Shuojia Dong, Montreal (CA); Danick Godin, St-Bruno-de-Montarville (CA); George Koutlakis, Greenfield Park (CA); Nicole Lachapelle, L'Assomption (CA); André Laforest, St-Amable (CA); Caroline Lavergne, Mascouche (CA); Vladimiro Nettel, Kirkland (CA); Nicolas Nourry, St-Amable (CA); Frédéric Picard, St-Jean-sur-Richelieu (CA); Oscar Suarez-Hernandez, Laval (CA); Catherine Theriault, St-Amable (CA)

(73) Assignee: Archer Daniels Midland Company, Decatur, IL (US)

( * ) Notice: Subject to any disclaimer, the term of this patent is extended or adjusted under 35 U.S.C. 154(b) by 444 days.

(21) Appl. No.: 11/861,081

(22) Filed: Sep. 25, 2007

(65) Prior Publication Data

US 2008/0177057 A1 Jul. 24, 2008

Related U.S. Application Data

(60) Provisional application No. 60/826,845, filed on Sep. 25, 2006, provisional application No. 60/912,471, filed on Apr. 18, 2007, provisional application No. 60/912,611, filed on Apr. 18, 2007, provisional application No. 60/912,623, filed on Apr. 18, 2007.

(51) Int. Cl.
| | |
|---|---|
| *A61K 31/715* | (2006.01) |
| *C08B 11/12* | (2006.01) |
| *B01D 15/00* | (2006.01) |
| *C08B 35/00* | (2006.01) |
| *C08B 31/16* | (2006.01) |

(52) U.S. Cl.
USPC .............. 514/54; 536/97; 536/98; 536/104; 536/108; 536/116; 127/49; 516/136

(58) Field of Classification Search
USPC ... 536/97, 98, 104, 108, 116; 514/54; 127/49; 516/136
See application file for complete search history.

(56) References Cited

U.S. PATENT DOCUMENTS

| | | | |
|---|---|---|---|
| 3,445,245 A | 5/1969 | Ebner | 426/17 |
| 3,489,719 A * | 1/1970 | Savage et al. | 525/385 |
| 4,076,844 A | 2/1978 | Ebner | 426/17 |
| 4,281,184 A | 7/1981 | Spaziante et al. | 562/603 |
| 4,282,257 A | 8/1981 | Kunimatsu et al. | 426/17 |
| 4,383,121 A | 5/1983 | Sugamiya et al. | 562/602 |
| 4,456,622 A | 6/1984 | Maselli et al. | 426/17 |
| 4,463,019 A | 7/1984 | Okuhara et al. | 426/17 |
| 4,503,078 A | 3/1985 | Ebner | 426/17 |
| 4,569,845 A | 2/1986 | Nodes | 426/17 |
| 4,656,140 A | 4/1987 | Yamada et al. | 436/131 |
| 4,935,360 A | 6/1990 | Klemps et al. | 435/140 |
| 5,079,354 A | 1/1992 | Gross et al. | 536/111 |
| 5,247,072 A | 9/1993 | Ning et al. | 536/97 |
| 5,470,964 A | 11/1995 | Qin | 536/20 |
| 5,498,705 A | 3/1996 | Qin | 536/20 |
| 5,550,189 A | 8/1996 | Qin et al. | 525/54.3 |
| 5,668,273 A * | 9/1997 | Allen et al. | 536/66 |
| 6,753,170 B2 | 6/2004 | Gaddy et al. | 435/140 |
| 6,765,042 B1* | 7/2004 | Thornton et al. | 523/400 |
| 7,135,597 B2 | 11/2006 | Crouzen et al. | 562/603 |
| 2004/0157734 A1 | 8/2004 | Mertens et al. | 502/401 |
| 2006/0147689 A1 | 7/2006 | Wallajapet et al. | 428/292.1 |
| 2006/0149182 A1 | 7/2006 | Cullen et al. | 602/49 |

FOREIGN PATENT DOCUMENTS

| | | |
|---|---|---|
| CA | 2308537 | 11/2000 |
| CA | 2362006 | 5/2002 |
| CA | 2462053 | 9/2004 |
| CA | 2483049 | 3/2005 |
| NL | 9100249 | 9/1992 |
| WO | WO 98/00558 | 1/1998 |
| WO | WO 00/35504 | 6/2000 |
| WO | WO 01/87365 | 11/2001 |

OTHER PUBLICATIONS

PCT International Search Report, issued in International Application No. PCT/CA2007/001734, dated Jan. 14, 2008.
Buchholtz et al., "Swelling Capacity: Theory and Practice," *Modern Superabsorbent Polymer Technology*, 147-165, 1998.
Stuiver et al., "Discussion reporting of 14C data," *Radiocarbon*, 19(3):355-363, 1977.

* cited by examiner

*Primary Examiner* — Wu-Cheng Winston Shen
*Assistant Examiner* — Everett White

(57) ABSTRACT

Surface-treated carboxyalkylated polysaccharides comprising a biobased content of at least 82% are described herein. The surface-treated carboxyalkylated polysaccharides comprise a CRC of at least 18 g/g, a FSC of at least 26 g/g, and an AUL at 0.7 psi of at least 14 g/g. Processes for the manufacture of surface-treated carboxyalkylated polysaccharides are also described herein.

17 Claims, 11 Drawing Sheets

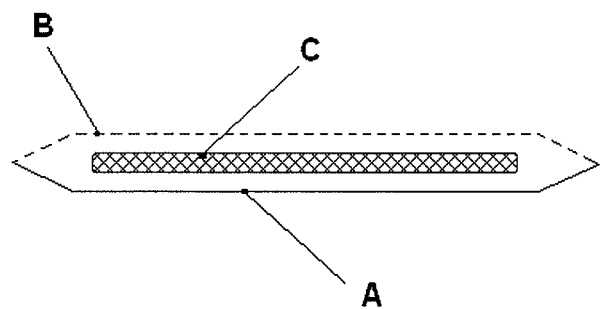
FIG. 1
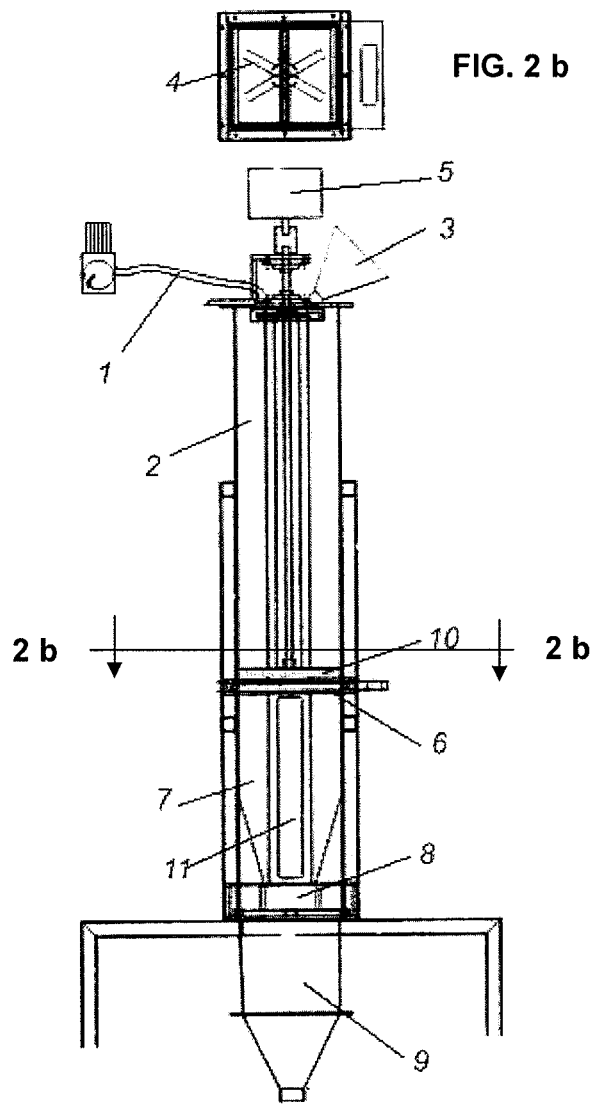
FIG. 2 b
FIG. 2 a

SUPERABSORBENT SURFACE-TREATED CARBOXYALKYLATED POLYSACCHARIDES AND PROCESS FOR PRODUCING SAME

CROSS REFERENCE TO RELATED APPLICATIONS

The present application claims the benefit of U.S. Provisional Application No. 60/826,845 filed on Sep. 25, 2006 and U.S. Provisional Applications 60/912,471; 60/912,611 and 60/912,623 filed on Apr. 18, 2007 the entire contents of which are incorporated by reference.

FIELD OF THE INVENTION

The present disclosure relates to superabsorbent surface-treated carboxyalkyl polysaccharides. More specifically, but not exclusively, the present disclosure also relates to a process for the manufacture of surface-treated carboxyalkyl polysaccharides having absorbent properties. The present disclosure also relates to formulations and hygiene articles comprising surface-treated carboxyalkyl polysaccharides.

BACKGROUND OF THE INVENTION

Water absorbent materials, such as superabsorbent polymers, can be employed in various applications such as in disposable hygiene articles (e.g. diapers, incontinence articles, feminine hygiene products airlaids and absorbent dressings); household articles; sealing materials; in oil-drilling fluids (e.g. lost-circulation material, fracturing fluids); anti-condensation coatings; in agricultural, horticultural and forestry applications for retaining water in the soil and for the release of water to the roots of plants and trees; in the textile industry; in printing applications; in absorbent paper products; in bandages and surgical pads (e.g. wound dressings); in ore treatments; in concrete products; in pet litter; in water treatment; in food pads (e.g. applications related to the transportation of fresh food and food packaging); in detergents; in fire-fighting gels; in cloud control; as chemical absorbents for the cleanup of acidic and/or basic aqueous spills including water soluble chemical spills; as polymeric gels for the slow and controlled release of cosmetics and pharmaceuticals (also known as drug delivery systems); and in the manufacture of artificial snow. However, the primary use of superabsorbent polymers, also referred as "SAPs", resides in disposable personal hygiene articles. Such products include, in decreasing order of volume of superabsorbent materials used, diapers, training pants, adult incontinence products and feminine hygiene products.

Carboxyalkyl polysaccharides have been disclosed as superabsorbent materials by Ning et al. U.S. Pat. No. 5,247,072; Qin et al. U.S. Pat. Nos. 5,470,964; 5,498,705; 5,550,189; WO 01/87365; and Wallajapet et al. US App. 2006/0147689. However, in addition to being costly, the absorption characteristics of such materials were often insufficient to be useful in the hygiene industry. As a result, synthetic superabsorbent materials such as polyacrylates have experienced rapid development.

The "Absorbency Under Load" (AUL), as measured at 0.7 psi, constitutes a widely recognized indicator characterizing to the absorption efficiency of a superabsorbent material. Carboxyalkyl polysaccharides exhibiting high AUL values have been previously disclosed by Mertens et al. (US App. 2004/0157734). However, Mertens is silent with respect to the biobased content and the carboxyalkylation pattern of the polysaccharides disclosed. Moreover, Mertens is silent with respect to the carboxyalkylation process used to manufacture the materials disclosed.

Carboxyalkylated starches, produced by means of aqueous processes, have been previously disclosed by Gross et al. U.S. Pat. No. 5,079,354; Couture et al. CA 2,362,006; and Theodorus et al. NL 9100249. However, the carboxyalkylated starches were not disclosed as having high AUL values.

The present disclosure refers to a number of documents, the content of which is herein incorporated by reference in their entirety.

SUMMARY OF THE INVENTION

The present disclosure broadly relates to surface-treated carboxyalkyl polysaccharide particles exhibiting superabsorbent properties.

In an embodiment, the present disclosure relates to superabsorbent surface-treated carboxyalkyl polysaccharides comprising a biobased content of at least 82% and which polysaccharides have an AUL (as measured at 0.7 psi) of at least 14 g/g. In an embodiment of the present disclosure, the surface-treated carboxyalkylated polysaccharides comprise a natural polymeric backbone of an agricultural origin.

In an embodiment of the present disclosure, the surface-treated carboxyalkylated polysaccharides comprise a particle ranging in size from 150 μm to 850 μm.

In an embodiment, the present disclosure relates to superabsorbent, internally cross-linked carboxyalkyl polysaccharide particles. In an embodiment of the present disclosure, the internally cross-linked carboxyalkyl polysaccharide particles are surface treated.

In an embodiment of the present disclosure, the carboxyalkylated polysaccharide is selected from the group consisting of carboxyalkylated starches, carboxyalkylated celluloses and carboxyalkylated galactomannans. Non-limiting examples of starches include potato, corn, wheat, waxy corn tapioca and mixtures thereof.

In yet a further embodiment, the present disclosure relates to surface-treated carboxymethyl starch. In an embodiment of the present the disclosure, the carboxymethyl starch comprises a homogeneous carboxymethyl substitution pattern and exhibits an AUL (as measured at 0.7 psi) of at least 14 g/g following surface treatment.

In yet a further embodiment, the present disclosure relates to a carboxyalkylated starch obtained by carboxyalkylation in an aqueous alkaline medium. In an embodiment, the carboxyalkylated starch is surface treated.

Moreover, in an embodiment, the present disclosure relates to a process for the manufacture of surface-treated carboxyalkylated polysaccharides comprising:
- obtaining a carboxyalkylated polysaccharide;
- surface-treating the carboxyalkylated polysaccharide using a non-cross-linking acid; and
- heating the surface-treated carboxyalkylated polysaccharide.

In an embodiment of the present disclosure, the heating source is selected from the group consisting of an infra-red source and a hot gas source.

In an embodiment of the present disclosure, the process may optionally comprise an internal cross-linking step, a particle size reducing step and/or a sieving step.

Moreover, in an embodiment, the present disclosure relates to a process for the manufacture of surface-treated carboxyalkylated starch comprising:
- dispersing starch in an alkaline medium;
- reacting the starch with a carboxyalkylating reagent;

surface-treating the carboxyalkylated starch using a non-cross-linking acid; and heating the surface-treated carboxyalkylated polysaccharide.

In an embodiment of the present disclosure, the heating source is selected from the group consisting of an infra-red source and a hot gas source.

In an embodiment of the present disclosure, the carboxyalkylating step further comprises, in a non-specific sequence: (i) adjusting the pH of the carboxyalkylated starch; (ii) purifying the carboxyalkylated starch; and (iii) adjusting the moisture content of the carboxyalkylated starch. Moreover, in an embodiment of the present disclosure, the process may optionally comprise an alkaline pre-slurrying step, an internal cross-linking step, a particle size reducing step and/or a sieving step. In an embodiment of the present disclosure, the pH of the carboxyalkylated starch ranges from 6.0 and 10.0.

Moreover, in an embodiment, the present disclosure relates to carboxyalkylated polysaccharide particles comprising an acidified surface. In a further embodiment of the present disclosure, these particles are characterized by the absence of an ester band or an ester shoulder as illustrated by ATR-IR spectroscopy.

Moreover, in an embodiment, the present disclosure relates to a carboxyalkylated polysaccharide comprising:

an acidic surface and;

internal cross-linking linkages selected from the group consisting of ionic and ether linkages;

wherein said carboxyalkylated polysaccharide is characterized by the presence of an ester band as illustrated by ATR-IR spectroscopy.

In yet a further embodiment, the present disclosure relates to a hygiene article and/or an absorbent member comprising surface-treated carboxyalkylated polysaccharide particles.

In yet a further embodiment, the present disclosure relates to an absorbent member comprising from about 15% to about 80% (W/W) of surface-treated carboxyalkyl polysaccharide particles. In a further embodiment of the present disclosure, the surface-treated carboxyalkyl polysaccharide particles comprise a biobased content of at least 82% (W/W) as determined by ASTM method D6866-06A. In yet a further embodiment, the present disclosure relates to a hygiene article comprising an absorbent as described hereinabove. In an embodiment of the present disclosure, the hygiene article comprises a third acquisition rate of at least 0.22 ml/second and/or an average acquisition rate of at least 0.12 ml/second. In an embodiment of the present disclosure, the hygiene article comprises a third rewet value of at most 4.0 grams and/or a total rewet value of at most 6.0 grams.

In yet a further embodiment, the present disclosure relates to the use of surface-treated carboxyalkyl polysaccharide particles as absorbents in disposable sanitary products (e.g. diapers, incontinence articles, feminine hygiene products, airlaids and absorbent dressings); household articles; sealing materials; in oil-drilling fluids (e.g. lost-circulation material, fracturing fluids); anti-condensation coatings; in agricultural, horticultural and forestry applications for retaining water in the soil and for the release of water to the roots of plants and trees; in the textile industry; in printing applications; in absorbent paper products; in bandages and surgical pads (e.g. wound dressings), in ore treatments; in concrete products; in pet litter; in water treatment; in food pads (e.g. applications related to the transportation of fresh food and food packaging); in detergents; in fire-fighting gels; in cloud control; as chemical absorbents for the cleanup of acidic and/or basic aqueous spills including water soluble chemical spills; as polymeric gels for the slow and controlled release of cosmetics and pharmaceuticals (also known as drug delivery systems), as airlaids; and in the manufacture of artificial snow.

In yet a further embodiment, the present disclosure relates to the use of surface-treated carboxyalkyl polysaccharide particles as absorbents for liquids. In an embodiment of the present disclosure, the liquids are selected from the group consisting of water, aqueous solutions, physiological fluids and saline solutions.

Finally, the present disclosure relates to compositions comprising surface-treated carboxyalkyl polysaccharide particles and a co-absorbent material.

The foregoing and other objects, advantages and features of the present disclosure will become more apparent upon reading of the following non restrictive description of illustrative embodiments thereof, given by way of example only with reference to the accompanying drawings.

BRIEF DESCRIPTION OF THE DRAWINGS

In the appended drawings:

FIG. 1 is a partially sectional schematic side elevational view of a hygiene article in accordance with an embodiment of the present disclosure;

FIG. 2a is a schematic side elevational view of an apparatus for manufacturing an absorbent member in accordance with an embodiment of the present disclosure; FIG. 2b is a cross-sectional view taken along line 2b-2b of FIG. 2a;

FIG. 3 is an enlarged schematic cross-sectional elevational view of the absorbent member forming cell of the apparatus of FIG. 2a;

DETAILED DESCRIPTION OF ILLUSTRATIVE EMBODIMENTS

Figure 3:
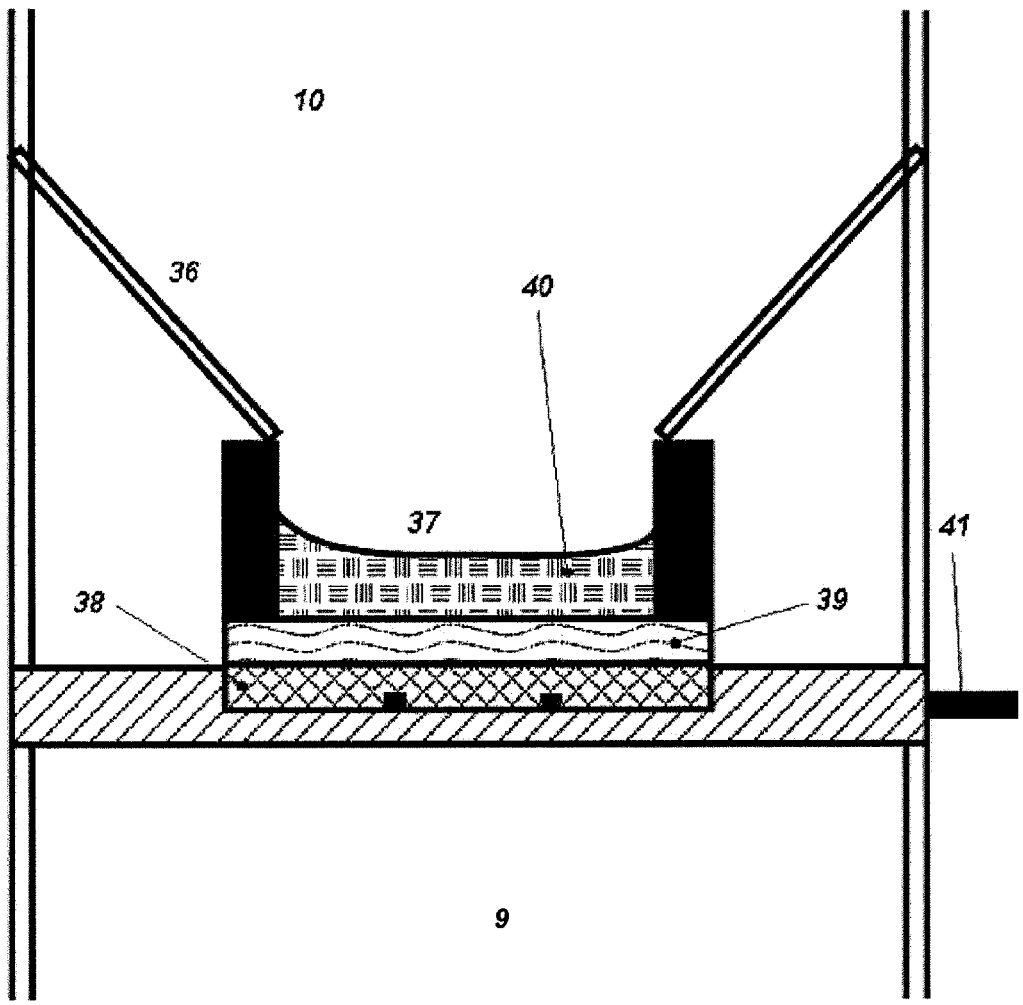

In order to provide a clear and consistent understanding of the terms used in the present specification, a number of definitions are provided below. Moreover, unless defined otherwise, all technical and scientific terms as used herein have the same meaning as commonly understood by one of ordinary skill in the art to which the present disclosure pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this specification and claim(s), the term "about" is defined as being close to as understood by one of ordinary skill in the art, and in one non-limiting embodiment the term is defined to be within 10%, preferably within 5%, more preferably within 1%, and most preferably within 0.5%.

The term "percent" or "%", unless otherwise specified, refers to a percentage by weight (i.e. % (W/W)).

As used in this specification, the term "saline solution" refers to a 0.9% (W/W) sodium chloride solution in deionized water.

As used in this specification, the term "discrete particle" refers to individual particles.

As used in this specification, the term "homogeneous substitution" refers to carboxyalkylated polysaccharides comprising a substantially uniform distribution of carboxyalkyl groups over most of the anhydroglucose units following carboxyalkylation. Typically, homogeneously substituted carboxyalkylated polysaccharides are characterized by a standard deviation in the substitution degree of at most 0.3.

As used in this specification, the term "polysaccharide" refers to polymers having a backbone comprising monosaccharide repeating units. Non-limiting examples include starches, modified starches, amylopectin, modified amylopectin, amylose, modified amylose, cellulose, modified cellulose, galactomannans and modified galactomannans.

As used in this specification, the term "monosaccharide unit" refers to cyclic $C_5$-$C_6$ aldoses or ketoses. Non limiting examples of $C_5$-$C_6$ aldoses include allose, altrose, glucose, mannose, gulose, idose, galactose, talose, ribose, arabinose, xylose, and lyxose. Non limiting examples of $C_5$-$C_6$ ketoses include ribulose, xylulose, fructose, sorbose and tagatose.

As used in this specification, the term "Free Swell Capacity" (FSC), also called "Total Absorption", refers to the amount (g) of fluid absorbed per gram of the composition. Typical fluids are saline solutions (0.9% Weight/Weight NaCl solution, hereinafter called 0.9% NaCl solution or saline).

As used in this specification, the term "Centrifuge Retention Capacity" (CRC) also called "Retention", refers to the amount (g) of fluid retained per gram of the composition, following exposure of the composition to a centrifugation force of 250 G. Typical fluids are saline solutions (0.9% Weight/Weight NaCl solution, hereinafter called 0.9% NaCl solution or saline).

As used in this specification, the term "Absorption Under Load" (AUL) at 0.7 PSI, also called "Absorption Against Pressure" (AAP) or "Absorption Under Pressure" (AUP) refers to the amount (g) of fluid absorbed per gram of the composition under a given applied pressure. Typical fluids are saline solutions (0.9% Weight/Weight NaCl solution, hereinafter called 0.9% NaCl solution or saline).

As used herein, the term "hygiene article" refers to products designed to absorb fluids, more specifically, physiological fluids. Non limiting examples of hygiene articles include diapers, incontinence garments and sanitary napkins.

As used herein, the term "absorbent core" refers to the component of the hygiene article that is primarily responsible for liquid handling properties of the article, including acquiring, transporting, distributing and storing body liquids.

As used herein, the term "absorbent member" refers to the component of the absorbent core that typically provides one or more liquid handling properties, e.g., liquid acquisition, liquid distribution, liquid transportation, liquid storage, etc.

The term "gelatinization" is well known in the art and is generally used to describe the swelling and hydration of starches.

As used herein, the term "rewet" or "wet-back" is a measure of the absorbent article's fluid retention capabilities under load. Rewet values are reported in grams.

As used in this specification, the term "absorbent material" or "absorbent polymer" refers to materials in a dry, solid state, having good fluid-swelling properties and capable of gel forming upon contact with a fluid. Non limiting examples of such fluids are water, aqueous solutions, saline, or physiological fluids.

As used in this specification, the term "superabsorbent", "superabsorbent polymer" or "SAP" refers to absorbent materials capable of gel forming upon contacting with a liquid such as water, aqueous solutions, saline, or physiological fluids. Such materials are characterized by a Centrifuge Retention Capacity (CRC) of at least 15 g/g.

As used in this specification, the term "moisture content" refers to the amount of water (% w/w) contained in a material.

As used in this specification, the term "aqueous" is meant to include any type of reaction medium comprising at least 15% by weight (W/W) of water. This includes, but is not limited to, systems comprising water and optionally one or more co-solvents.

As used in this specification, the term "granular material", "granules", "particles", "powders", "grains" or "dusts" refers to particulate matter in a finely divided state.

As used in this specification, the term "particle size" refers to the largest dimension of a particle. The particle size can be directly determined using sieving methods, optical or scanning electron microscopes as well as by other well-known methods. The particle size is often considered as diameter of the particle.

As used in this specification, the term "discrete gel particles" refers to superabsorbent particles which, once sufficiently swollen in saline solution, have the appearance of discrete hydrogel particles.

As used in this specification, the term "surface treated" refers to a chemically or physically modified surface.

As used in this specification, the term "cross-linking agent", "cross-linker" or "exogenous cross-linking agent" refers to an agent which in combination with a cross-linkable polysaccharide reacts with the polysaccharide to produce a cross-linked polysaccharide. Non-limiting examples of cross-linking reactions include the reaction of the cross-linking agent with a least two polysaccharide hydroxyl groups; the reaction of the cross-linking agent with a least two polysaccharide carboxyl groups; and the reaction of the cross-linking agent with a polysaccharide hydroxyl group and a polysaccharide carboxyl group.

As used in this specification, the term reaction efficiency (R.E.) generally refers to the amount (%) of product obtained; relative to theoretical amount based on the initial amount of reagents used.

Very few naturally occurring biopolymers possess adequate gel forming properties. Biopolymers typically produce gels that, when wet, will form an impermeable layer blocking the flow of fluids. Moreover, their structural strength is low, rendering them ineffective for applications requiring high AUL characteristics. Modification of the biopolymer structure frequently results in undesired reductions of the biobased content. Polysaccharides comprise a class of biopolymer that has been previously used in the absorbent industry. Non-limiting examples of polysaccharides include galactomannans, starches and celluloses.

Starch is widely known for its gel forming properties in hot water. Starch-based absorbents have been previously disclosed by Huppé et al. CA U.S. Pat. No. 2,308,537 and Thibodeau et al. CA U.S. Pat. No. 2,462,053. However, these materials were not disclosed as having adequate AUL characteristics. It was surprisingly discovered that surface-treated carboxyalkylated starches possess good AUL characteristics, making them suitable as superabsorbent materials in the personal hygiene industry.

Starches can be obtained from a variety of sources, including but not limited to corn, wheat, potato, yam, cassava, rice, millet, sorghum, barley, oats, beans, fava beans, peas, lentils, buckwheat, bananas, arracacha, oca, sago, taro, tapioca, sweet potatoes and mixtures thereof. In an embodiment of the present disclosure, the starches are obtained from a waxy species of, but not limited to, corn, wheat, potato, yam, cassava, rice, millet, sorghum, barley, oats, beans, fava beans, peas, lentils, buckwheat, bananas, arracacha, oca, sago, taro, tapioca, sweet potatoes and mixtures thereof. In an embodiment of the present disclosure, the starch is obtained from sources selected from the group consisting of corn, waxy corn, potato, tapioca and wheat.

In order to improve the AUL characteristics, the polysaccharides are chemically modified by reaction with a carboxyalkylating agent. In an embodiment of the present disclosure, the carboxyalkylating agent comprises a carboxymethylating agent. The carboxyalkyl groups may be either in their neutral carboxylic form or in the form of carboxylate ions. As a result of their strongly ionic character, carboxyalkylated polysaccharides exhibit strong osmotic forces. An osmotic driving force is beneficial for obtaining high absorption capacities.

In an embodiment, the carboxyalkylated polysaccharides of the present disclosure comprise a pH ranging from 4.5 to 10.0. In a further embodiment, the carboxyalkylated polysaccharides of the present disclosure comprise a pH ranging from 5.0 to 8.0. The pH of the carboxyalkylated polysaccharides influences any subsequent surface-treatment reactions.

Non limiting examples of cations associated with the carboxyalkylated polysaccharides of the present disclosure, include monovalent cations such as sodium, potassium, ammonium ions and organic ammonium ions. In an embodiment of the present disclosure, the cation comprises silver. Silver has been previously described as exhibiting anti-microbial properties (Cullen et al. US 2006/0149182 A1). Superabsorbents comprising silver carboxymethyl starches are useful as odor inhibiting agents as well as for controlling bacterial growth. Moreover, silver carboxymethyl starches are suitable for use in wound dressings and surgical drapes.

In an embodiment of the present disclosure, the carboxyalkylated polysaccharides are prepared by Williamson ether synthesis. In an embodiment of the present disclosure, the carboxyalkylating agent comprises haloacids and/or salts thereof. Non-limiting examples of salts include alkali metal salts. In a further embodiment of the present disclosure, the haloacids comprise $C_2$-$C_5$ haloacids. In yet a further embodiment of the present disclosure, the $C_2$-$C_5$ haloacids comprise monochloroacetic acid, sodium monochloroacetate, potassium monochloroacetate, lithium monochloroacetate and mixtures thereof.

A typical carboxyalkylation reaction is as follows:

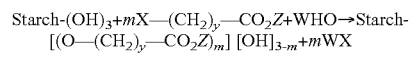

wherein:

Y is an integer ranging from 1 to 4; X is selected from the group consisting of Cl, Br and I; W is an alkali metal; m is a numerical value ranging from 0.3 to 1.5; and Z is selected from the group consisting of H, alkali metal, ammonium and organic ammonium.

In an embodiment of the present disclosure, the carboxyalkylated polysaccharides comprise biobased-derived carboxyalkyl substituents. In an embodiment of the present disclosure, the substituents are derived from biobased haloacids and/or salts thereof. In yet a further embodiment of the present disclosure, the biobased haloacid comprises monochloroacetic acid. Acetic acid and glycolic acid intermediates are obtained from biobased substrates by fermentation or oxidation (U.S. Pat. Nos. 4,463,019; 4,456,622; 4,569,845; 3,445,245; 4,076,844; 4,282,257; 6,753,170; WO 98/00558; U.S. Pat. Nos. 4,935,360; 4,656,140; and 4,503,078). The intermediates can be halogenated as described in U.S. Pat. Nos. 4,281,184; 4,383,121; 7,135,597.

In an embodiment of the present disclosure, the carboxyalkylating agent comprises non-biobased haloacids or mixtures thereof with biobased haloacids and/or salts thereof.

In an embodiment, the present disclosure relates to carboxyalkylated polysaccharides comprising a biobased substitution degree of at least 0.01. In an embodiment, the present disclosure relates to carboxyalkylated polysaccharides comprising a total degree of substitution ranging from 0.2 to 1.0. In a further embodiment, the present disclosure relates to carboxyalkylated polysaccharides comprising a total degree of substitution ranging from 0.4 to 0.7.

Alkaline Medium and Carboxyalkylation

The carboxyalkylation of starch was performed by first dispersing the starch in an alkaline medium. In an embodiment of the present disclosure, the starch is dispersed directly in dry alkali. Alternatively, the starch can be dispersed in an aqueous alkaline organic hydrophilic solvent. In an embodiment of the present disclosure, the organic hydrophilic solvent comprises a $C_1$-$C_5$ alcohol. Non-limiting examples of dry alkali comprise lithium hydroxide, sodium hydroxide, potassium hydroxide and mixtures thereof. In an embodiment of the present disclosure, the dry alkali are in powder form. In an embodiment of the present disclosure, the $C_1$-$C_5$ alcohol is isopropanol.

Surprisingly, when the carboxyalkylation process was performed in an alkaline aqueous medium, superior absorbent characteristics were obtained for the carboxyalkylated product. Without being bound to any theory, it is believed that the starch chains and the carboxyalkylating agents are more labile in an aqueous environment. This increased mobility provides for a more homogeneous carboxyalkylated substitution pattern. In an embodiment of the present disclosure, the aqueous alkaline medium comprises a pH of at least 11.0. Typical starch moisture contents range from 15% to 99%. The propensity for side reactions between the hydroxyl functions and the carboxyalkylating agent increase with increasing moisture content.

Surprisingly, when the carboxyalkylation process was performed using reactive extrusion, products exhibiting superior absorbent characteristics (AUL at 0.7 psi of at least 14 g/g) were obtained. Moreover, reaction efficiencies of at least 60% could be obtained by reactive extrusion. In an embodiment of the present disclosure, the water content in the carboxyalkylation-extrusion process ranges from 15% to 30%.

Twin screw extruders are typically used to perform the carboxyalkylation process. Twin screw extruders provide for the added flexibility and the shear required to perform the carboxyalkylation reaction. In an embodiment of the present disclosure, dry ingredients such as starch and the carboxyalkylating agent were fed into the extruder. The ingredients were the conveyed to an alkali (e.g. alkali hydroxide) injection point, typically located upstream the kneading elements. The alkali may be injected in the form of a solution. Water may be optionally injected to ensure a moisture content ranging from 15% to 30%. In order to limit reagent degradation in the extruder, the temperature is kept below 140° C. The resulting alkaline paste is pumped and kneaded in order to increase the reaction efficiency. The twin screw extruder may be optionally equipped with a vent providing for the evacuation of moisture. The vent may be placed under vacuum if increased moisture evacuation is desired. The carboxyalkylated starch may be optionally pumped into a die to produce extrudate strands.

In an embodiment of the present disclosure, the carboxyalkylated polysaccharides are cross-linked. The cross-linking may be performed before, during or after the carboxyalkylation process. In an embodiment of the present disclosure, the cross-linking is performed before the carboxyalkylation step. A slurry is typically obtained when starch is mixed with water. The slurry-like state is maintained upon the addition of small amount of alkali (pH≦10). The alkaline slurry provides for a suitable reaction medium for the reaction of starch with a covalent cross-linking agent. In an embodiment of the present disclosure, the cross-linking agent comprises epichlorohydrin. Performing the cross-linking prior to the gelatinization step provides for increased cross-linking reaction efficiency. In an embodiment, the present disclosure relates to cross-linked carboxyalkylated polysaccharides having a cross-linker content (based on carboxyalkylated polysaccharide) of at most 10%. In a further embodiment, the present disclosure relates to cross-linked carboxyalkylated starch having a cross-linker content (based on carboxyalkylated starch) of at most 10%.

Cross-linking provides for a starch product having increased molecular weight, increased gel strength and increased resistance to deformation under stress. An increase in gel strength will result in increases in CRC and AUL. In an embodiment of the present disclosure, cross-linked polysaccharides having a molecular weight of at least 500,000 Da were used.

In an embodiment, the present disclosure relates to carboxyalkylated polysaccharides characterized by a FSC of at least 25 g/g, a CRC of at least 18 g/g and an AUL at 0.7 Psi of at least 14 g/g.

Purification

The purity of the carboxyalkylated product is of importance. As important amounts of salt are produced during the carboxyalkylation step, any residual impurities may lead to "salt poisoning", which will have the effect of reducing the absorption performance of the carboxyalkylated product. The carboxyalkylated product can be purified by washing with a water miscible organic solvent and/or water miscible organic solvent/water mixtures. Non-limiting examples of water miscible organic solvents include $C_1$-$C_4$ alcohols. The washed carboxyalkylated product is subsequently filtered and dried. The purification process is continued until no further salt precipitation can be observed from the washings when mixed with $AgNO_3$. The conductivity of the washings represents a further indication of the purity of the carboxyalkylated product. The conductivity should be at most 1,500 µS/cm.

In an embodiment of the present disclosure, the carboxyalkylated product was purified under acidic conditions. The first step typically comprises an acidification procedure. The carboxylate groups were converted into carboxylic groups. The acidified carboxyalkylated polysaccharides will typically exhibit a pH ranging from 4.5 to 6.5. The acidified carboxyalkylated product was then heated, as the heated product is substantially insoluble in water. Instead, the product will swell and form a hydrogel or hydrogel particles. The gel particles were subsequently washed with water, or acidic solutions, to remove any residual salts. The purification process was continued until no further salt precipitation could be observed from the washings when mixed with $AgNO_3$. The conductivity of the washings represents a further indication of the purity of the carboxyalkylated product. The conductivity should be at most 1,500 µS/cm.

Adjusting pH and Moisture

In order to obtain a suitable carboxylate content, the pH of the purified carboxyalkylated polysaccharide may be adjusted to be within 6.0 to 10.0. In an embodiment of the present disclosure, the pH may be adjusted in water miscible organic solvents.

Reactive extrusion may also be used to adjust the pH of the carboxyalkylated polysaccharide. In an embodiment of the present disclosure, the pH is adjusted following the carboxyalkylation reaction but before the extruder discharge. The pH can be adjusted by injecting an acidic solution into the carboxyalkylated polysaccharide paste. In an embodiment of the present disclosure, the paste comprises a carboxyalkylated starch. The acidified paste mixture was subsequently conveyed and pumped into a section of the extruder comprising a further series of kneading elements, accomplishing the pH adjustment of the polysaccharide product. Following the pH adjustment, the product was conveyed, pumped and discharged from the extruder. The twin screw extruder may be optionally equipped with a vent providing for the evacuation of moisture. The vent may be placed under vacuum if increased moisture evacuation is desired. The product may be optionally pumped into a die to produce extrudate strands.

The moisture content of the carboxyalkylated product may be further adjusted. In an embodiment of the present disclosure, the moisture content of the carboxyalkylated product is of at most 7%. Non-limiting examples of moisture lowering techniques comprise conduction heating, vacuum evaporation, convection heating and infra-red heating. It is believed to be within the capacity of a skilled technician to select other suitable moisture lowering techniques.

Particle Formation

In an embodiment of the present disclosure, the carboxyalkylated polysaccharides comprise a particulate matter. In a further embodiment of the present disclosure, the carboxyalkylated starches comprise a particulate matter. In yet a further embodiment of the present disclosure, the carboxyalkylated starches are "glass-like". In yet a further embodiment of the present disclosure, the carboxyalkylated starches comprise a "porous" structure. The particulate structure of the carboxyalkylated product is influenced by the pH adjustment, the purification procedure and the moisture adjustment. The particulate structure of the carboxyalkylated product will also influence the bulk density, frangibility and abrasiveness. In an embodiment, the carboxyalkylated starch product of the present disclosure comprises a bulk density ranging from 0.5 g/cm$^3$ to 0.7 g/cm$^3$.

In an embodiment of the present disclosure, the size of the carboxyalkylated polysaccharide particles is reduced. Sieving comprises a convenient technique to control the particle size. The absorption performance of the carboxyalkylated polysaccharide particles is linked to their particle size. Particles having a size of at least about 150 μm (100 Mesh) will limit gel blocking. Particles having a size of at most about 850 μm (20 Mesh) will limit pinhole formation in hygiene products and will swell more efficiently.

Surface Coating

Under high pressures, such as 0.7 psi, gel particles will have a tendency to collapse and form "disc-shaped" gel particles. These "disc-shaped" particles will severely impede the absorption process and may eventually lead to gel blocking. More rigid gel particles will provide increased resistance to deformation and will maintain an adequate swelling rate. Surface treated carboxyalkylated polysaccharide particles exhibit absorbent properties (FSC, CRC) similar to lightly cross-linked carboxyalkylated polysaccharides, while having enough structural rigidity to swell under pressure (AUL).

Surface treatment agents will decrease the water solubility of the surface of the carboxyalkylated polysaccharide particles. Moreover, surface treatment agents will give to the carboxyalkylated polysaccharides, once swollen, the appearance of discrete gel particles. Surface treatment will also increase the AUL at 0.7 Psi. Surface treatments are typically effected upon heating. Non-limiting examples of surface treatment agents include cross-linkers, non-cross-linking acids and combinations thereof. Non-limiting examples of non-cross-linking acids include monovalent acids. These acids may be derived from mineral sources, from non-bio-based sources or from biobased sources. In an embodiment of the present disclosure, the non-cross-linking acids are selected from the group consisting of hydrochloric acid, acetic acid, glycolic acid and stearic acid.

Higher AUL values (at 0.7 Psi) are typically obtained with increased surface-treatment. However, care should be taken to not adversely affect other important SAP characteristics such as the FSC and CRC. In an embodiment of the present disclosure, the amount of non-crosslinking acid reagent ranges from about 0.01 milliequivalent to about 20.0 milliequivalents per gram of carboxyalkylated polysaccharide (meq/g). In a further embodiment of the present disclosure, the pH of the surface-treated carboxyalkylated polysaccharide ranges from about 4.5 to 6.5.

In an embodiment of the present disclosure, the surface of the carboxyalkylated polysaccharides is treated with a cross-linking agent. Non-limiting examples of cross-linking agents include citric acid, aluminum ions ($Al^{3+}$) and epichlorohydrin. Treatment with citric acid will result is the formation of ester linkages; treatment with epichlorohydrin will result in the formation of ether linkages; and treatment with aluminum ions. In a further embodiment of the present disclosure, the pH of a citric acid surface-treated carboxyalkylated polysaccharide ranges from about 4.5 to 6.5.

In an embodiment of the present disclosure, the surface treatment is performed by treating the surface of the carboxyalkylated polysaccharides with a solution comprising the surface treatment agent. In order to achieve an adequate particle surface treatment, the penetration depth of the surface treatment agent should be carefully controlled. Such control can be achieved by the careful selection of an appropriate solvent system. Non-limiting examples of such solvent systems include hydrophilic organic solvents and hydrophilic organic solvent/water mixtures. The use of an organic hydrophilic solvent will limit surface treatment agent diffusion and surface swelling of the carboxyalkyl polysaccharide particles. Typical hydrophilic organic solvents comprise $C_1$-$C_5$ alcohols. In an embodiment of the present disclosure, the hydrophilic organic solvent comprises isopropanol. In an embodiment of the present disclosure, hydrophilic organic solvent/water mixtures are used. In a further embodiment of the present disclosure, the mixture comprises a solvent/water ratio ranging from 50/50 to 95/5. The water in these mixtures provides for increased surface penetration.

In an embodiment of the present disclosure, the carboxyalkylated polysaccharide particles are mixed with the solvent having dissolved therein the surface treatment agent. A wet powder or a paste is typically obtained. The paste or wet powder may optionally be comminuted prior to heating. Prior to heat treatment, the solvent may optionally be evaporated. The solvent evaporation step is typically performed at temperatures of not more than 100° C.

In an embodiment of the present disclosure, the surface treatment was performed by applying droplets of a solution comprising the surface treatment agent to the surface of the carboxyalkylated polysaccharide particles. Non-limiting examples of solvent systems include hydrophilic organic solvents and hydrophilic organic solvent/water mixtures. It was surprisingly discovered that aqueous solutions are suitable under such conditions. In order to avoid particle swelling, the aqueous solution should be rapidly evaporated following droplet application. In an embodiment of the present disclosure, evaporation was achieved by means of gas circulation around the particles. In a further embodiment of the present disclosure, the gas has a temperature of at least 40° C. Particle swelling is substantially avoided when the droplet application flow is at least equivalent to the solvent evaporation rate. Such an environment can be achieved in an agglomerator or on a fluidized bed dryer equipped with spraying nozzles.

Heat Treatment

Most surface treatment agents require a heating step. Surface treatment results in a product exhibiting good AUL values (at 0.7 psi).

The heat treatment may be accomplished using an electromagnetic radiation source, a hot gas or a heated surface. In an embodiment of the present disclosure, convection (hot gas) or Infra-Red (electromagnetic radiation) heating is used. Typically, IR sources identified as medium infra-red or carbon infra-red are well suited. In an embodiment of the present disclosure, the surface treated carboxyalkylated polysaccharides are heated to temperatures of at least 140° C. In a further embodiment of the present disclosure, the surface treated carboxyalkylated polysaccharides are heated to temperatures of at least 160° C. In yet a further embodiment of the present disclosure, the moisture content of the surface treated carboxyalkylated polysaccharide particles following heat treatment is less than 5%. Care should be taken not to overheat the particles. Overheating is typically characterized by browning of the particles.

In an embodiment of the present disclosure, the heat treatment was accomplished in a static environment. Non-limiting examples of static environments include immobile environments, belt-conveyed environments, sliding environments or any environment that substantially avoids inducing undue interaction (i.e. shearing) between the particles themselves or between the particles and other objects. In an embodiment of the present disclosure, the static environment comprises a surface over which the particles are evenly spread. Such a surface is typically an IR transmitting surface such as glass or Pyrex™.

Figure 6:
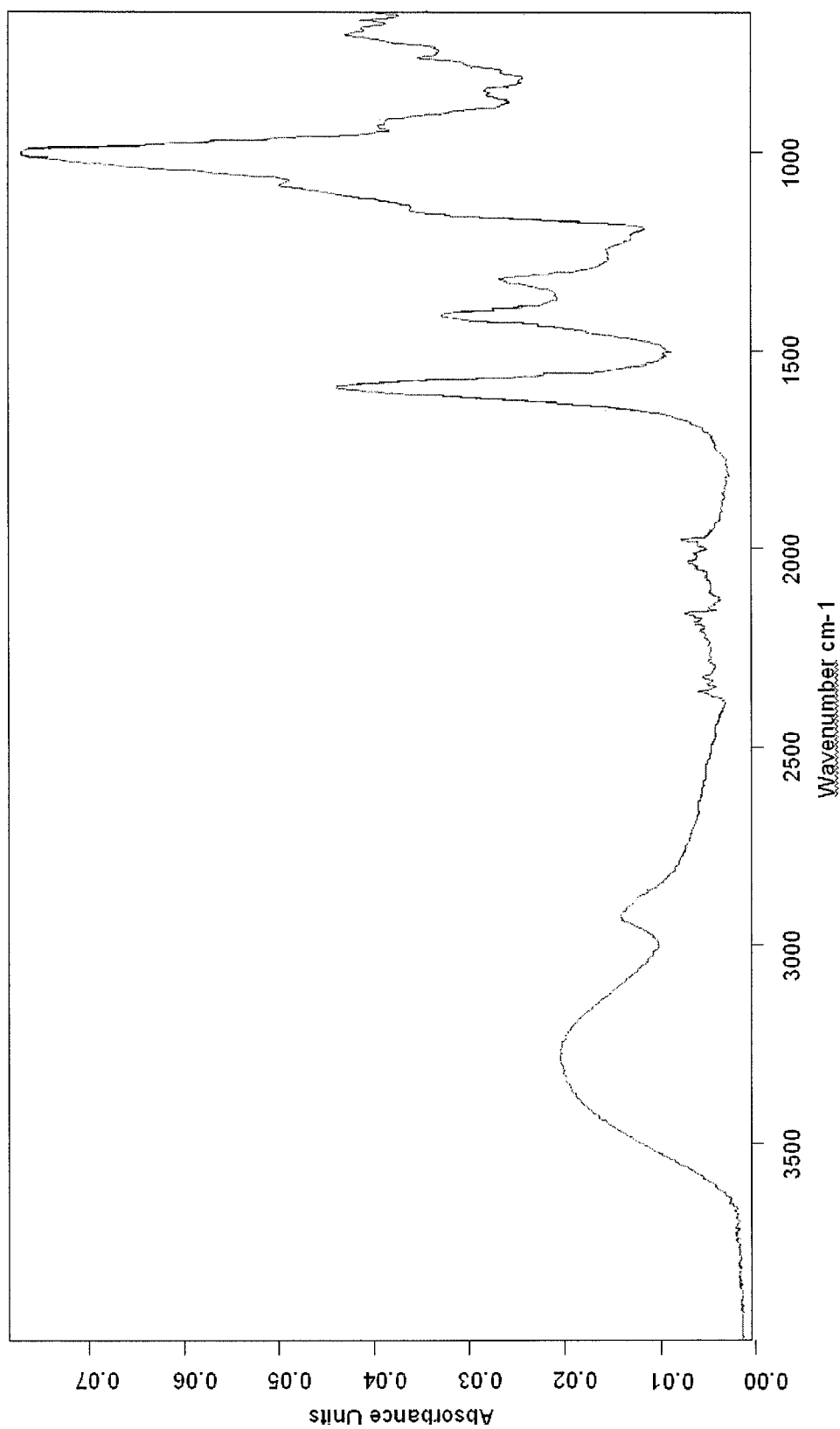
FIG. 6 shows an attenuated total reflectance infra-red spectrum (ATR-IR) of hydrochloric acid surface-treated carboxyalkylated starches in accordance with an embodiment of the present disclosure.
Figure 7:
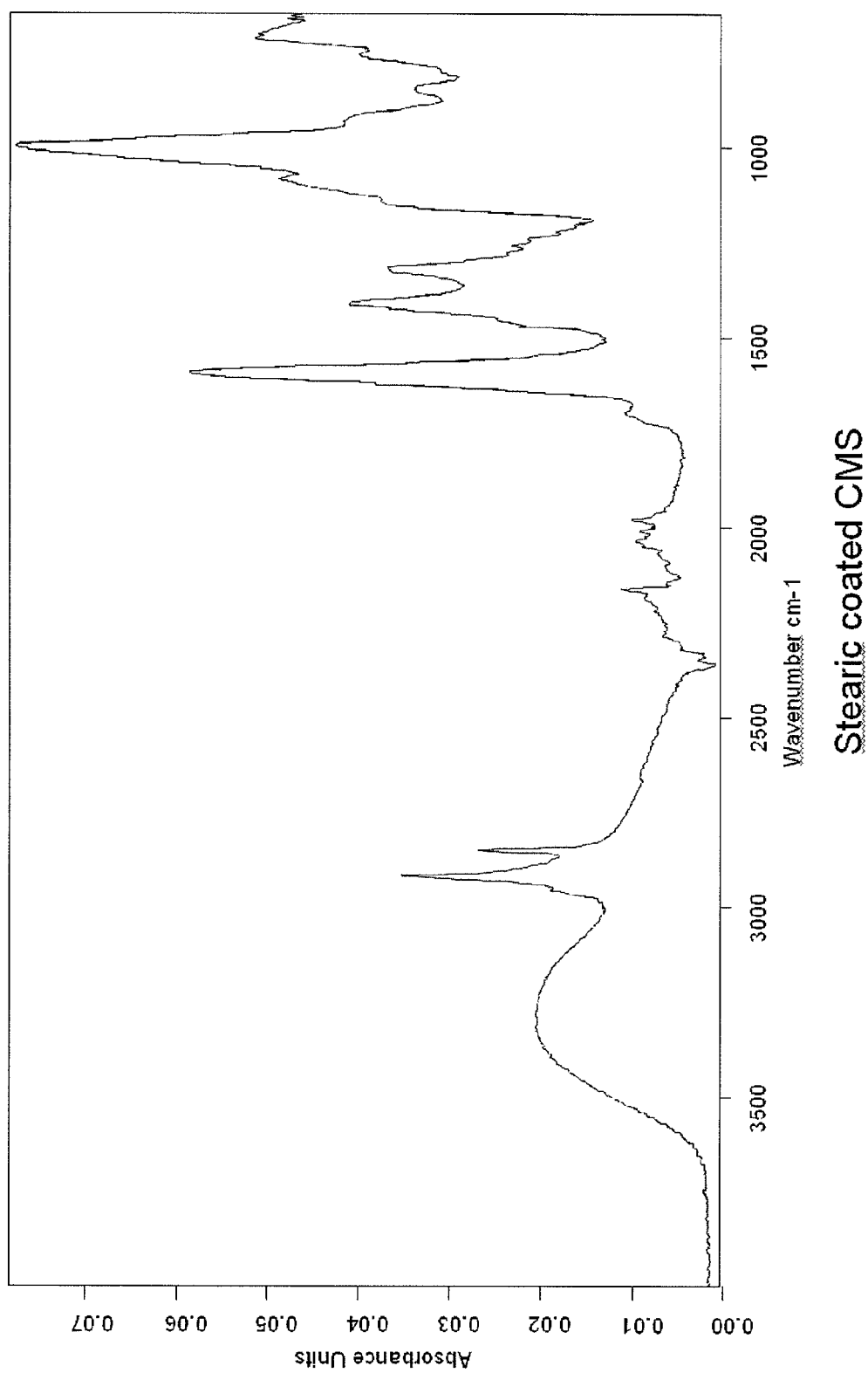
FIG. 7 shows an attenuated total reflectance infra-red spectrum (ATR-IR) of stearic acid surface-treated carboxyalkylated starches in accordance with an embodiment of the present disclosure.

The carboxyalkylated polysaccharides of the present disclosure may be surface treated with may types of acids. When non-crosslinking acids are used, ester linkages are typically not observed by ATR-IR spectroscopy. The absence of an ester band (between 1750 cm$^{-1}$ and 1715 cm$^{-1}$) was noted in the case of hydrochloric acid surface treated carboxyalkylated starches (FIG. 6). The presence of a shoulder was observed for stearic acid surface treated carboxyalkylated starches (FIG. 7).

In an embodiment, the present disclosure relates to internally cross-linked carboxyalkylated polysaccharides. These polysaccharides may also be surface-treated by exposure to surface treating agents.

In an embodiment of the present disclosure, the surface-treated carboxyalkylated starches have an AUL at 0.7 Psi of at least 14 g/g. In an embodiment of the present disclosure, the surface-treated carboxyalkylated starches have an AUL at 0.7 Psi of at least 14 g/g and a CRC of at least 18 g/g. In an embodiment of the present disclosure, the surface-treated carboxyalkylated starches have an AUL at 0.7 Psi of at least 14 g/g, a CRC of at least 18 g/g and a FSC of at least 25 g/g. In a further embodiment of the present disclosure, the surface-treated carboxyalkylated starches are characterized by a bulk density ranging from 0.5 g/cm$^3$ to 0.7 g/cm$^3$.

The surface-treated carboxyalkylated polysaccharides form discrete gel particles once swollen. The propensity to form discrete gel particles makes these materials especially suitable for use in hygiene articles. Indeed, when incorporated into absorbent members, discrete gel particles upon swelling to their maximum extend, provide for enhanced water flow. This characteristic significantly increases the wet porosity of the absorbent articles and thus improved liquid absorption and diffusion.

In an embodiment of the present disclosure, the surface-treated carboxyalkylated starches have an AUL at 0.7 Psi of at least 14 g/g and a biobased content, according to ASTM D 6866-06 A, of at least 82%. In an embodiment of the present disclosure, the surface-treated carboxyalkylated starches have an AUL at 0.7 Psi of at least 14 g/g and a biobased content, according to ASTM D 6866-06 A, of at least 87%. In an embodiment of the present disclosure, the surface-treated carboxyalkylated starches have an AUL at 0.7 Psi of at least 14 g/g and a biobased content, according to ASTM D 6866-06 A, of at least 95%. These surface-treated carboxyalkylated starches are suitable for use in hygiene articles and absorbent members.

The surface-treated carboxyalkylated polysaccharides of the present disclosure may be mixed with other co-absorbent materials to provide absorbent compositions. In an embodiment, the absorbent compositions comprise from about 1 to about 99% (w/w) of surface-treated carboxyalkylated polysaccharides and from about 99 to about 1% (w/w) of co-absorbent material. Non-limiting examples of co-absorbent materials include synthetic absorbent polymers, starch-based absorbents, mannose containing polysaccharides, fibers and mixtures thereof.

The surface-treated carboxyalkylated starch of the present disclosure may be mixed with other co-absorbent materials to provide absorbent compositions. In an embodiment, the absorbent compositions comprise from about 1 to about 99% (w/w) of surface-treated carboxyalkyl starches, and from about 99 to about 1% (w/w) of co-absorbent material. Non-limiting examples of co-absorbent materials include synthetic absorbent polymers, starch-based absorbents, mannose containing polysaccharides, fibers and mixtures thereof.

Non-limiting examples of starch-based absorbents include glass-like starches such as disclosed by Huppé et al. (CA 2,308,537); amylopectin networks such as disclosed by Thibodeau et al. (CA 2,462,053); polysaccharide agglomerates such as disclosed by Chevigny et al. (CA 2,534,026); hydroxyethyl starch; hydroxypropyl starch; starch nanocomposites such as disclosed by Berrada et al. (CA 2,483,049); and mixtures thereof.

Non-limiting examples of mannose containing polysaccharides include guar gum, tara gum, locust bean gum, konjac, mesquite gum, psyllium extracts, fenugreek extracts and mixture thereof. The mannose containing polysaccharides may be chemically or enzymatically modified (i.e. mannose derivatives), cross-linked or in the form of nanocomposite materials.

Non-limiting examples of fibers include cellulose, viscose, rayon, cellulose acetate, polyamides (i.e. Nylon™), polyalkylenes, polyethylene, polypropylene, bi-component fibers, polyesters, polylactides, polypropanediols, polyhydroxyalkanoates, Lyocell™, sphagnum and mixtures thereof.

The synthetic absorbent polymers to be used as co-absorbent materials in the absorbent compositions of the present disclosure, are generally obtained from the polymerization, typically by radical or radical graft polymerization, of monomers, non-limiting examples of which include acrylic acid, acrylate salts, acrylic ester, acrylic anhydride, methacrylic acid, methacrylate salts, methacrylic esters, methacrylic anhydride, maleic anhydride, maleic salts, maleate esters, acrylamide, acrylonitrile, vinyl alcohol, vinyl pyrrolidone, vinyl acetate, vinyl guanidine, aspartic acid, aspartic salts and mixtures thereof.

The surface-treated carboxyalkylated polysaccharide particles of the present disclosure, or compositions comprising such particles, are suitable for use in methods for absorbing liquids. In an embodiment of the present disclosure, one or more of the surface-treated-carboxyalkylated polysaccharides are contacted with a liquid to be absorbed. Non-limiting examples of liquids include water, aqueous solutions, physiological fluids and saline solutions. The surface-treated carboxyalkylated polysaccharides of the present disclosure, upon contacting with the liquid(s) to be absorbed, will form a gel trapping the liquid(s) within.

The surface-treated carboxyalkylated starch particles of the present disclosure, or absorbent compositions comprising such particles, are suitable for use in methods for absorbing liquids. In an embodiment of the present disclosure, one or more of the surface-treated-carboxyalkylated starches are contacted with a liquid to be absorbed. Non-limiting examples of liquids include water, aqueous solutions, physiological fluids and saline solutions. The surface-treated carboxyalkylated starches of the present disclosure, upon contacting with the liquid(s) to be absorbed, will form a gel trapping the liquid(s) within.

These surface-treated carboxyalkylated polysaccharides of the present disclosure are suitable for use in hygiene articles, including diapers, incontinence products and sanitary napkins. In an embodiment of the present disclosure, the surface-treated carboxyalkylated polysaccharide is a surface-treated carboxyalkylated starch. A typical hygiene article is illustrated in FIG. 1. The article comprises a backsheet A, a topsheet B and an absorbent core C. The absorbent core is typically disposed between the top- and bottom sheets. The top- and bottom sheets may provide a sealing envelope for the absorbent core. The backsheet is typically an impermeable film composed of a plastic material. The topsheet is typically a porous, water permeable, water insoluble, film or non-woven material. An acquisition distribution layer (non-illustrated) may optionally be disposed between the topsheet and the absorbent core. The acquisition-distribution layer provides for the diffusion of liquids into the absorbent core, increasing both the stain area and the absorption speed.

The absorbent member constitutes the component of the absorbent core that is responsible for absorbing urine and physiological fluids when used in the context of hygiene articles. In an embodiment of the present disclosure, the absorbent members comprise cellulose fluff pulp fibers and surface-treated carboxyalkylated polysaccharides. The components can be uniformly mixed in an air-dispersion. The absorbent members may optionally further comprise additives such as fragrances, odor control agents, binders, thermoplastic fibers, cross-linkers and fillers. In an embodiment of the present disclosure, the absorbent members are compressed in order to reduce their bulkiness. In a further embodiment of the present disclosure, the absorbent members have a density of at least 0.10 $g/cm^3$. In an embodiment, the absorbent members of the present disclosure comprise a surface-treated carboxyalkylated polysaccharide content ranging from 15% to 80%. In a further embodiment, the absorbent members of the present disclosure comprise a surface-treated carboxyalkylated polysaccharide content ranging from 30% to 60%.

The hygiene articles comprising the absorbent members of the present disclosure exhibit surprisingly good absorbent characteristics. The surface-treated carboxyalkylated polysaccharides, as contained within the absorbent members, are characterized by a biobased content, according to ASTM D 6866-06 A, of at least 82%. The averaged and third acquisition rates are widely accepted indicators when assessing the absorbency characteristics of a hygiene article. In an embodiment of the present disclosure, the hygiene articles comprise a third acquisition rate of at least 0.22 ml/sec and an averaged acquisition rate of at least 0.12 ml/sec. The third rewet and the total rewet comprise indicators for assessing the quality of a hygiene article. In an embodiment of the present disclosure, the hygiene articles comprise a third rewet value of at most 4.0 g. In a further embodiment of the present disclosure, the hygiene articles comprise a third rewet value of at most 1.5 g. In an embodiment of the present disclosure, the hygiene articles comprise a total rewet value of at most 6.0 g. In a further embodiment of the present disclosure, the hygiene articles comprise a total rewet value of at most 2.5 g.

The surface-treated carboxyalkylated polysaccharides of the present disclosure may also be used in other applications such as in food pads; in agricultural, horticultural and forestry applications for retaining water in the soil and for the release of water to the roots of plants and trees; in the textile industry; in printing applications; in absorbent paper products; in ore treatments; in concrete additives; in pet litter; in water treatment; in cloud control; in drilling fluids (e.g. lost circulation materials, fracturing fluids); in food pads (e.g. applications related to the transportation of fresh food and food packaging); in detergents; anti-condensation coatings; in fire-fighting gels; in sealing materials; in bandages and surgical pads (e.g. wound dressings); as chemical absorbents for the cleanup of acidic and/or basic aqueous spills including water soluble chemical spills; as polymeric gels for the slow and controlled release of cosmetics and pharmaceuticals (also known as drug delivery systems), and finally in the manufacture of artificial snow.

EXPERIMENTAL

Materials

Potato starch was obtained from Penford Food Ingredients (Centennial, Colo.). Grade A wheat starch (Whetstar™ 4) was obtained from Archer Daniels Midland (Decatur, Ill.). Epichlorohydrin, sodium monochloroacetate, citric acid monohydrate, stearic acid, acetic acid, research grade isopropanol and sodium hydroxide were obtained from Sigma-Aldrich (St-Louis, Mo.). Hydrochloric acid and methanol was obtained from Labmat (Quebec City, Canada).

Infra-Red Thermometer

A TES 1326S infra-red thermometer was used.

Convection Oven

A Lab tray drier TY 2, National Drying Machinery Company, (Philadelphia, USA) was used.

Infra-Red Oven

A Panasonic NB-G100P infra-red oven was used.

Grinder

A Braun™ model KSM grinder was used to grind the samples.

Extruder (CMC)

A Baker-Perkins MPF-50D (50 mm) twin screw extruder was used to manufacture CMC hydrogels. The extruder was equipped with a ME-II Accurate Power Feeder. An injection nozzle was positioned 381 mm downstream the extruder. No die was used. The extruder had the following screw design:

TABLE 1

TSE Screw Design

| Element type | Element length (mm) |
|---|---|
| Beginning | |
| Spacer | 6.35 |
| Spacer | 101.6 |
| Conveying | 76.2 |
| Pumping | 50.8 |
| Kneading | 12.7 |
| Pumping | 50.8 |
| Conveying | 76.2 |
| Pumping | 50.8 |
| Pumping | 25.4 |
| Exit Port | |

Extruder (CMS)

In an embodiment of the present disclosure, a Leistritz ZSE 40 HP (40 mm) twin screw extruder was used to manufacture carboxyalkylated polysaccharides. The extruder L/D ration was set at 40. The polysaccharide (e.g. starch) was fed into the TSE using an Acrison gravimetric agitated feeder (405-170-OE). Sodium monochloroacetate was fed into the TSE using an Acrison gravimetric feeder (405-1015-C). Starch and sodium monochloroacetate were into the TSE at positions located between 30 mm and 180 mm downstream the extruder. A sodium hydroxide injection nozzle, equipped with a Cole-Parmer peristaltic pump, was positioned 560 mm downstream the extruder. Closed side stuffer barrels were positioned at a location between 640 mm and 800 mm downstream the extruder. A vent was positioned at a location between 1120 mm and 1280 mm downstream the barrel. No die was used. The extruder had the following screw design:

TABLE 2

TSE Screw Design

| Pitch length (mm) | Element length (mm) | Kneading block angle (°) |
|---|---|---|
| Extruder's beginning | | |
| 20 mm | 30 mm | |
| 60 mm | 150 mm | |
| 30 mm | 60 mm | |
| 45 mm | 150 mm | |
| 45 mm | 150 mm | |
| 45 mm | 50 mm | |
| 45 mm | 50 mm | |
| 30 mm | 60 mm | |
| Kneading block 6 elements (forward) | 60 mm | 60° |
| Kneading block 6 elements (forward) | 60 mm | 60° |
| 45 mm | 30 mm | |
| 45 mm | 60 mm | |
| Kneading block 6 elements | 60 mm | 90° |
| Kneading disc | 10 mm | |
| Kneading disc | 10 mm | |
| 60 mm | 150 mm | |
| 45 mm | 150 mm | |
| 45 mm | 60 mm | |
| 45 mm | 60 mm | |
| Extruder's discharge | | |

All extruder elements were double flighted. The kneading element thickness was 2 mm.

Agglomerator

A STREA-1 model from Niro Pharma Systems (Fluid bed laboratory unit), equipped with a film coater nozzle, was used. The STREA-1 model was configured with the injection nozzle located laterally; the nozzle facing upside down.

Apparatus Used to Manufacture the Absorbent Member

FIG. 2a illustrates an apparatus for the manufacture of an absorbent member. Fluff pulp fibers and surface-treated carboxyalkylated polysaccharide were conveyed into the apparatus and deposited on a non-woven filter using a high velocity air stream. The air stream was provided using a compressor (790 KPa) connected to the apparatus through a flexible hose (1). A pressurized air regulator was connected to the compressor. Fluff pulp fibers and surface-treated carboxyalkylated polysaccharides (e.g. surface treated carboxyalkylated starch) are introduced into a first mixing chamber (2) of the absorbent-core forming apparatus using a funnel (3). The fluff pulp fibers and the surface-treated carboxyalkylated polysaccharide (e.g. surface treated carboxyalkylated starch) were thoroughly mixed in the mixing chamber using a 6-bladed propeller (4) connected to an electric motor (5). The propeller was located above a 4-Mesh screen (6). In an embodiment of the present disclosure, the propeller was located 59 mm above the 4-Mesh screen (6). A brush (10) was positioned above the screen; the brush rubbing against the screen. Particles small enough to pass through the screen were transported to a second mixing chamber (7) using an air flow, from which they were conveyed into an absorbent member-forming cell (8) (illustrated in greater detail in FIG. 3). An air vacuum chamber (9) was positioned underneath the absorbent member-forming cell (8). The vacuum chamber (9) was connected to a vacuum cleaner (not shown). The absorbent member-forming process can be observed through a visualization window (11).

FIG. 3 illustrates an enlarged view of the absorbent member-forming cell. A funnel (36) was positioned over a molding cell (37) in which the absorbent member (40) was produced. A 20-Mesh screen (38) was positioned at the bottom of the molding cell (37). A Maquin S.A. 20 g/m² non-woven filter (39) was positioned between the molding cell (37) and the screen (38) for retaining fine fluff and fine polysaccharide particles. Air passing through the molding cell (37) was conveyed to a vacuum chamber (9). Upon completion of the process, the molding cell (37) was removed using a handled plate (41).

Rewet Cylinder

Figure 4:
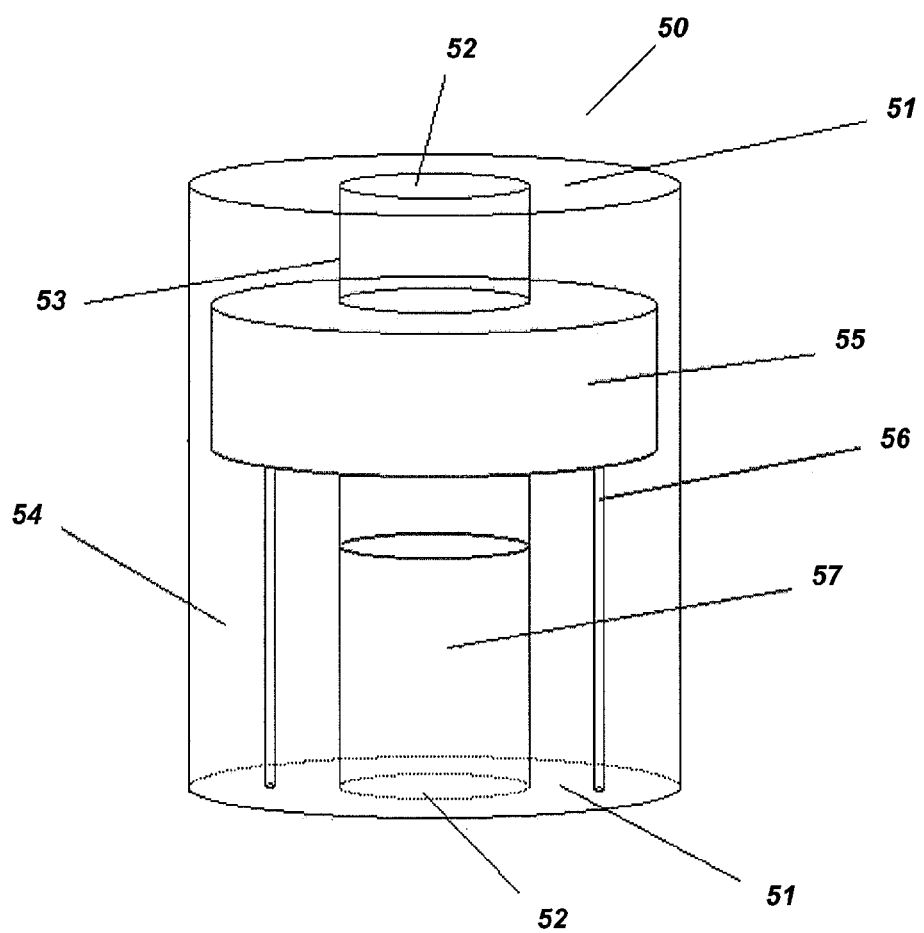
FIG. 4 is a schematic perspective view of a rewet cylinder for testing the absorbent members or hygiene articles of the present disclosure.

FIG. 4 illustrates a rewet cylinder (50) for testing the rewet characteristics of the absorbent members or hygiene articles of the present disclosure. The opposing ends (10 cm diameter) (51) of the cylinder were composed of Plexiglas™ and contained a central orifice (52) measuring 2.5 cm in diameter. The opposing ends of the cylinder had a surface area of 78.5 cm². An inner co-axial cylinder (53) is disposed within the rewet cylinder (50) defining a cylindrical space (54) therebetween. A weight (55), supported by two screws (56), was disposed within the cylindrical space (54). In an embodiment of the present disclosure, the rewet cylinder (50) weighed 3.87 kg. In operation, the inner cylinder (53) was filed with water (57).

Test Methods

As discussed in Modern Superabsorbent Polymer Technology (Buchholz, F. L. and Graham, A. T. Eds., Wiley-VCH, N.Y., 1998, section 4.6.1. Swelling Capacity: Theory and Practice, p. 147), several measurement methods are used to characterize the swelling capacity of a polymer. In the field of superabsorbents, the Gravimetric Swelling Capacity [also called the Free Swell Capacity (FSC)] and the Centrifuge Capacity [also called the Centrifuge Retention Capacity (CRC)] are recommended methods. The FSC and the CRC were used to characterize the swelling capacities of the absorbent products of the present disclosure.

Tea Bags for FSC and CRC Measurements

Tea bags (10×10 cm) were made from heat sealable Ahlstrom (Chirnside Duns, UK) filter paper (16.5±0.5 g/m²) grade 07291.

FSC Measurements

The Free Swell Capacity (FSC) in a 0.9% NaCl solution was determined according to the recommended test method WSP 240.2 (05) A from Worldwide Strategic Partners (EDANA-INDA).

CRC Measurements

The Centrifuge Retention Capacity (CRC) in a 0.9% NaCl solution was determined according to the recommended test method WSP 241.2 (05) A from Worldwide Strategic Partners (EDANA-INDA).

AUL Measurements

The Absorption Under Load (AUL) at 0.7 Psi, in a 0.9% NaCl solution was determined according to the recommended test method WSP 242.2 (05) A from Worldwide Strategic Partners (EDANA-INDA).

Biobased Content

The biobased content of the surface-treated carboxyalkylated polysaccharides of the present disclosure was determined by characterization of the modern radiocarbon content. Radiocarbon concentrations are provided as fractions of the modern standard $d^{14}C$, following the conventions of Stuiver and Polach (Radiocarbon, v.19, p. 355, 1977). All results have been corrected to account for isotopic fractionation according to the conventions of Stuiver and Polach (1977), with $d^{13}C$ values measured on prepared graphite using an AMS spectrometer. These values can differ from the $d^{13}C$ values obtained for the original material, if fractionation occurred during sample graphitization or the AMS measurement. Because the biobased content is given as "pre-bomb values", all ratios were multiplied by 93 (100% ×0.93) to reflect biobased percentages.

A precise amount (between 5 to 10 mg) of surface-treated carboxyalkylated polysaccharide was collected and transferred into a quartz tube comprising metallic silver and cupric oxide. The quartz tube was placed under vacuum, sealed and combusted at 850° C. over a period of 1 hour. The furnace was cooled (1° C./minute), until the sample was at 400° C.

The carbon dioxide product was then purified. In an embodiment of the present disclosure, the purification is accomplished by placing the quartz tube in a sealed tube cracker (as illustrated in ASTM D 6866-06A) under vacuum. The tube cracker was then immersed in a Dewar comprising liquid nitrogen. The tube was cryogenically cracked, allowing any unfrozen gases to escape. An alcohol/dry ice mixture was then placed around the tube cracker, sublimating the carbon dioxide content. The sublimated carbon dioxide was then transferred into a stainless steel tube (volume known) possessing a stopper. This stopper was closed and other gases were allowed to escape from the tube cracker. The stainless steel tube was then connected to a vacuumed Pyrex™ tube. The stainless steel tube was allowed to reach room temperature and the pressure observed. The carbon dioxide was allowed to enter the Pyrex™ tube. The bottom portion of the Pyrex™ tube was immerged in liquid nitrogen and the top portion sealed. The tubes were sent to an AMS facility for determination of the $^{14}C$ ratios.

Scanning Electron Micrographs

Scanning electron micrographs were recorded using a Hitachi® S 3000N scanning electron microscope. Samples were placed on two-sided adhesive paper, glued to an aluminum plate. Any non-glued particles were removed using an air jet. A thin (about 10 nm) gold layer was then applied to the surface of the glued sample using a sputter coater. The surface was then scanned and recorded.

Prototype Hygiene Article Manufacture

Hygiene articles were prepared by a process using the absorbent member forming apparatus (FIGS. 2 and 3). Bleached sulphate fluff pulp (8.5 g, SoLoNo™, Weyerhaeuser, Fereral Way, Wash.) was humidified in a room having a relative humidity ranging from 65% to 80%. The fluff pulp was divided into four portions (1.425 g; 2.360 g; 2.360 g; and 2.360 g).

A 10×20 cm thermobonded polypropylene non-woven (17 g/m², Industrias Maquin S.A., Puebla, Mexico) filter was positioned at the bottom of the molding cell (10×20 cm). The molding cell was assembled and positioned in the absorbent member forming apparatus. Following the creation of a vacuum in the vacuum chamber, the motor was switched on. The pressurized air regulator was activated, allowing pressurized air to enter the apparatus (60 Psi, 7/64 Nozzle). The first fluff portion (1.425 g) was added using a funnel, followed by the addition of surface-treated carboxyalkylated polysaccharide (1.860 g) twenty seconds later. Following a delay of 10 seconds, the second fluff portion (2.360 g) was added, followed by the addition of a further portion of surface-treated carboxyalkylated polysaccharide (1.860 g) twenty seconds later. Again, following a delay of 10 seconds, the third fluff portion (2.360 g) was added, followed by the addition of a further portion of surface-treated carboxyalkylated polysaccharide (1.860 g) twenty seconds later. Finally, following a delay of 10 seconds, the fourth fluff portion (2.360 g) was added and the apparatus shut-down 20 seconds later.

The molding cell was slowly removed from the absorbent member forming apparatus. The non-woven-fluff-surface-treated carboxyalkylated polysaccharide mixture was placed under a fitted (10×20 cm) hydraulic press, while remaining in the molding cell. The mixture was compressed using a force ranging from ½ to 1½ tons (4.9 kN to 14.7 kN) over a period of two minutes. In an embodiment of the present disclosure, following the compression, an absorbent member having a thickness ranging from about 6.71 mm to about 7.4 mm, a density of about 0.10 g/cm³, and a surface-treated carboxyalkylated starch content of about 39.7% was obtained. In order to simulate a hygiene article topsheet, a further 10×20 cm thermobonded polypropylene non-woven (17 g/m², Industrias Maquin S.A., Puebla, Mexico) filter was placed over the absorbent member. A laminated polyethylene film (20 g/m², Bonlam S.A., San-Luis-Potosi, Mexico) was placed on the other side of the absorbent member to simulate the absorbent backsheet. The absorbent members were then stockpiled in columns ranging from 4 to 6 items and sandwiched between Plexiglas plates applying a pressure of 0.7 psi over a period of 20 minutes.

Rewet Testing and Acquisition Rate Testing

The size of the prototype hygiene articles is small compared to commercial "size 4" baby diapers (user size ranging from 7 to 18 kg). The amount of fluids used in the testing was adopted to the smaller size of the prototype articles (50 ml/30 ml/30 ml). For larger scale testing (size 4), larger volumes of fluids are used (100 ml/60 ml/60 ml).

A prototype hygiene article was positioned on a flat surface and the center (7/12 $^{th}$ of the length) was marked with a permanent marker. A round Plexiglas™ test cylinder (FIG. 4) was then placed over the mark and charged with saline solution (50 ml). The chronometer was started as soon as the solution came into contact with the hygiene article. The chronometer was stopped as soon as all of the solution had disappeared from the surface of the hygiene article; the elapsed time was denoted as $T_1$. The hygiene article was allowed to equilibrate over a period of 20 minutes. The cylinder was subsequently removed and the wet surface covered with weighed filter papers (about 15 g, VWR West-Chester, USA, #28320-041 filter #415). An external pressure (0.7 PSI) was then applied using a circular stainless steel weight (3.13 Kg) having a surface area of 63.6 cm². Alternatively, any weight providing a pressure of 0.7 PSI or 4.83 KPa may be used. The pressure was maintained for 2 minutes. The increase in weight of the filter papers corresponds to the amount of fluid released by the hygiene article and was denoted as the first rewet.

The cylinder was then replaced and centered over the mark. The cylinder was charged with an additional amount of saline solution (30 ml) and the chronometer was started as soon as the solution came into contact with the hygiene article. The chronometer was stopped as soon as all of the solution had disappeared from the surface of the hygiene article; the elapsed time was denoted as $T_2$. The hygiene article was allowed to equilibrate over a period of 20 minutes. The cylinder was subsequently removed and the wet surface covered with weighed filter papers (about 15 g, VWR West-Chester, USA, #28320-041 filter #415). An external pressure (0.7 PSI) was then applied using a circular stainless steel weight (3.13 Kg) having a surface area of 63.6 cm². The pressure was maintained for 2 minutes. The increase in weight of the filter papers corresponds to the amount of fluid released by the hygiene article and was denoted as the second rewet.

The cylinder was then replaced and centered over the mark. The cylinder was charged with an additional amount of saline solution (30 ml) and the chronometer was started as soon as the solution came into contact with the hygiene article. The chronometer was stopped as soon as all of the solution had disappeared from the surface of the hygiene article; the elapsed time was denoted as $T_3$. The hygiene article was allowed to equilibrate over a period of 20 minutes. The cylinder was subsequently removed and the wet surface covered with weighed filter papers (about 15 g, VWR West-Chester, USA, #28320-041 filter #415). An external pressure (0.7 PSI) was then applied using a circular stainless steel weight (3.13 Kg) having a surface area of 63.6 cm². The pressure was maintained for 2 minutes. The increase in weight of the filter papers corresponds to the amount of fluid released by the hygiene article and was denoted as the third rewet. The total rewet corresponds to the sum of the individual rewet measurements.

The acquisition rate corresponds to the number of milliliters of saline solution absorbed by the hygiene article, divided by the time taken to absorb the volume of saline solution. The third acquisition rate can be calculated as follows: 30 ml/$T_3$=$A_3$ (ml/sec).

The averaged acquisition rate corresponds to the total number of milliliters of saline solution absorbed by the hygiene article (110 ml), divided by the total time taken to absorb the volume of saline solution. The averaged acquisition rate can be calculated as follows: 110 ml/($T_1+T_2+T_3$)=$A_T$ (ml/sec).

EXAMPLES

Citric Acid Surface-Treated Carboxymethyl Potato Starch

Water (900 ml), potato starch (297 g; 14% moisture content) and sodium hydroxide (5.6 g; 50% solution) were added to a two-liter beaker. The mixture was stirred over a period of 35 minutes at a temperature of 40° C. Epichlorohydrin (1.197 g) was subsequently added and the mixture allowed to react for an additional 35 minutes while stirring to produce a cross-linked starch slurry. Additional sodium hydroxide (192 g; 50% solution) was added and the slurry stirred for 5 minutes producing a gelatinized starch. The gelatinized starch was heated at 60° C. and mixed with sodium monochloroacetate (252 g; added stepwise over a period of 15 minutes). The gel was left to react for a period of 1 hour, precipitated by the addition of methanol (~7.0 liters) and filtered. The resulting precipitate was slurried in a methanol/water solution (2.0 liters; 9:1 V/V), the pH adjusted to 8.5-9.0 using hydrochloric acid and heated. The slurry was filtered, the residue re-slurried in a methanol/water solution (2.0 liters; 9:1 V/V) and filtered. An aliquot (1 ml) of the filtrate was taken and mixed with a few drops of silver nitrate. The absence of a silver chloride precipitate is indicative of product purity. Where a silver chloride precipitate was observed, the product was re-slurried again using a methanol/water solution (2.0 liters; 9:1 V/V) and filtered. This process was repeated until no further sliver chloride precipitation could be observed. The residue was subsequently purified by washing with methanol (2.0 liters), filtered and dried in a convection oven at 65° C.

Figure 5:
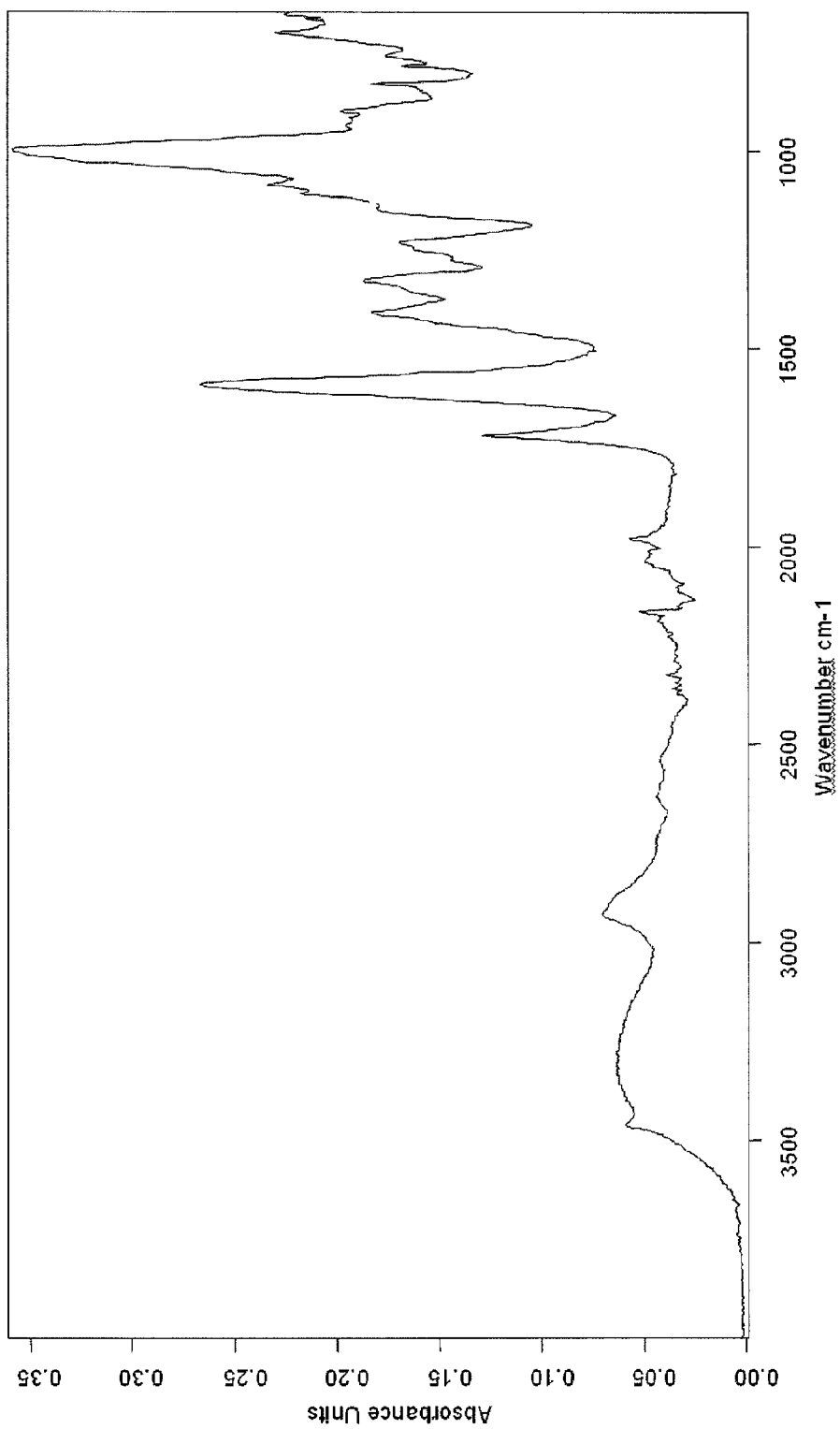
FIG. 5 shows an attenuated total reflectance infra-red spectrum (ATR-IR) of citric acid surface-treated carboxymethyl starch in accordance with an embodiment of the present disclosure.

The dried product (300 g) was dispersed in water (2.7 liters) to form a hydrogel. The pH of the hydrogel was adjusted to 8.5-9.0. The hydrogel was subsequently dried in a convection oven at 65° C. The dried product was ground and sieved (20 and 100 Mesh). The sieved product (40 g) was mixed with a citric acid solution (18.0 ml; 2.58 g of citric acid in 12 ml of water and 105 ml of isopropanol). The cake was evenly spread on a Pyrex™ pie dish (about 23 cm in diameter) having an even depth of about 1 mm. This cake was subsequently heated in convection mode at 100° C. over a period of 19 minutes. Further heating was accomplished in an IR oven at 140° C. over a period of 15 minutes. The absorbent characteristics of the resulting product were subsequently measured and are summarized hereinbelow in Table 3. The ATR-IR spectrum of the product is shown in FIG. 5.

TABLE 3

| Absorbent characteristics of citric acid surface-treated CMS | |
|---|---|
| FSC | 34.5 g/g |
| CRC | 25.0 g/g |
| AUL (0.7 psi) | 15.9 g/g |
| Biobased content | 82.2% |

Hygiene articles comprising the product (citric acid surface-treated CMS) were subsequently prepared and tested (Table 4).

TABLE 4

| Hygiene article performance | |
|---|---|
| Third rewet | 1.2 g |
| Total rewet | 1.7 g |
| Third acquisition rate | 0.25 ml/sec |
| Averaged acquisition rate | 0.14 ml/sec |

Number of hygiene articles tested: 16; results represent averaged values.

Acid Surface-Treated Carboxymethyl Potato Starch

Water (900 ml), potato starch (297 g; 14% moisture content) and sodium hydroxide (5.6 g; 50% solution) were added to a two-liter beaker. The mixture was stirred over a period of 35 minutes at a temperature of 40° C. Epichlorohydrin (1.197 g) was subsequently added and the mixture allowed to react for an additional 35 minutes while stirring to produce a cross-linked starch slurry. Additional sodium hydroxide (192 g; 50% solution) was added and the slurry stirred for 5 minutes producing a gelatinized starch. The gelatinized starch was heated at 60° C. and mixed with sodium monochloroacetate (252 g; added stepwise over a period of 15 minutes). The gel was left to react for a period of 1 hour, precipitated by the addition of methanol (~7.0 liters) and filtered. The resulting precipitate was slurried in a methanol/water solution (2.0 liters; 9:1 V/V), the pH adjusted to 8.5-9.0 using hydrochloric acid and heated. The slurry was filtered, the residue re-slurried in a methanol/water solution (2.0 liters; 9:1 V/V) and filtered. An aliquot (1 ml) of the filtrate was taken and mixed with a few drops of silver nitrate. The absence of a silver chloride precipitate is indicative of product purity. Where a silver chloride precipitate was observed, the product was re-slurried again using a methanol/water solution (2.0 liters; 9:1 V/V) and filtered. This process was repeated until no further sliver chloride precipitation could be observed. The residue was subsequently purified by washing with methanol (2.0 liters), filtered and dried in a convection oven at 65° C.

The dried product (300 g) was dispersed in water (2.7 liters) to form a hydrogel. The pH of the hydrogel was adjusted to 8.5-9.0. The hydrogel was subsequently dried in a convection oven at 65° C. The dried product was ground and sieved (20 and 100 Mesh). The sieved product (15 g) was mixed with an acidic solution (18.0 ml; 2.58 g of citric acid in 12 ml of water and 105 ml of isopropanol). For the preparation of the hydrochloric acid solution, hydrochloric acid (3,046 ml, 12N) was mixed with isopropanol (105 ml) and water (12 ml). For the preparation of the stearic acid solution, stearic acid (10.48 g) was dissolved in isopropanol (105 ml) and water (12 ml). For the preparation of the acetic acid solution, glacial acetic acid (2.21 g) was dissolved in isopropanol (105 ml) and water (12 ml). The cake was evenly spread on a Petri dish (about 9 cm in diameter) having an even depth of about 1 mm. This cake was subsequently heated in convection mode at 100° C. over a period of 15 minutes. Further heating was accomplished in an IR oven at 140° C. over a period of 12 minutes. The absorbent characteristics of the resulting product were subsequently measured and are summarized hereinbelow in Table 5.

TABLE 5

Absorbent characteristics of acid surface-treated CMS

| | Hydrochloric acid | Stearic acid | Acetic acid |
| --- | --- | --- | --- |
| FSC | 30.0 g/g | 31.5 g/g | 31.3 g/g |
| CRC | 18.0 g/g | 22.3 g/g | 21.1 g/g |
| AUL (0.7 psi) | 18.0 g/g | 11.9 g/g | 12.3 g/g |
| ATR-IR Figure | FIG. 6 | FIG. 7 | |

Comparison Between Dynamic and Static Heat Treatment Environments

Water (900 ml), waxy corn starch (297 g; 14% moisture content) and sodium hydroxide (2.8 g; 50% solution) were added to a two-liter beaker. The mixture was stirred over a period of 35 minutes at a temperature of 40° C. Epichlorohydrin (1.197 g) was subsequently added and the mixture allowed to react for an additional 35 minutes while stirring to produce a cross-linked starch slurry. Additional sodium hydroxide (192 g; 50% solution) was added and the slurry stirred for 5 minutes producing a gelatinized starch. The gelatinized starch was heated at 60° C. and mixed with sodium monochloroacetate (252 g; added stepwise over a period of 15 minutes). The gel was left to react for a period of 1 hour, precipitated by the addition of methanol (~7.0 liters) and filtered. The resulting precipitate was slurried in a methanol/water solution (2.0 liters; 9:1 V/V), the pH adjusted to 8.5-9.0 using hydrochloric acid and heated. The slurry was filtered, the residue re-slurried in a methanol/water solution (2.0 liters; 9:1 V/V) and filtered. An aliquot (1 ml) of the filtrate was taken and mixed with a few drops of silver nitrate. The absence of a silver chloride precipitate is indicative of product purity. Where a silver chloride precipitate was observed, the product was re-slurried again using a methanol/water solution (2.0 liters; 9:1 V/V) and filtered. This process was repeated until no further sliver chloride precipitation could be observed. The residue was subsequently purified by washing with methanol (2.0 liters), filtered and dried in a convection oven at 65° C.

The dried product (100 g) was dispersed in water (900 ml) to form a hydrogel. The pH of the hydrogel was adjusted to 8.5-9.0. The hydrogel was subsequently dried in a convection oven at 65° C. The dried product was ground and sieved (20 and 100 Mesh).

Dynamic Environment

The sieved product (7.5 g) was mixed with a citric acid solution (18.0 ml; 2.58 g of citric acid in 12 ml of water and 105 ml of isopropanol). The resulting slurry was placed in a round bottom flask equipped with a magnetic stirrer and heated over a period of 2 hours at a temperature of 90° C. The resulting slurry was subsequently heated with stirring over a period of 30 minutes at 140° C. Finally, the product was allowed to cool. The absorbent characteristics of the resulting product were subsequently measured and are summarized hereinbelow in Table 6.

Static Environment

The sieved product (5.0 g) was mixed with a citric acid solution (2.3 ml; 2.58 g of citric acid in 12 ml of water and 105 ml of isopropanol). The resulting slurry was placed on a watch glass and transferred into a convection oven where it was heated at 100° C. over a period of 10 minutes. The watch glass was subsequently placed into a humidity balance, equipped with an IR source and heated at 140° C. over a period of 30 minutes. Finally, the product was allowed to cool. The absorbent characteristics of the resulting product were subsequently measured and are summarized hereinbelow in Table 6.

TABLE 6

Absorbent characteristics of citric acid surface-treated CMS

Figure 8:
FIG. 8 shows a Scanning Electron Microscope (SEM) micrograph of dynamic surface-treated "glass-like" carboxymethyl starch particles in accordance with an embodiment of the present disclosure.
Figure 9:
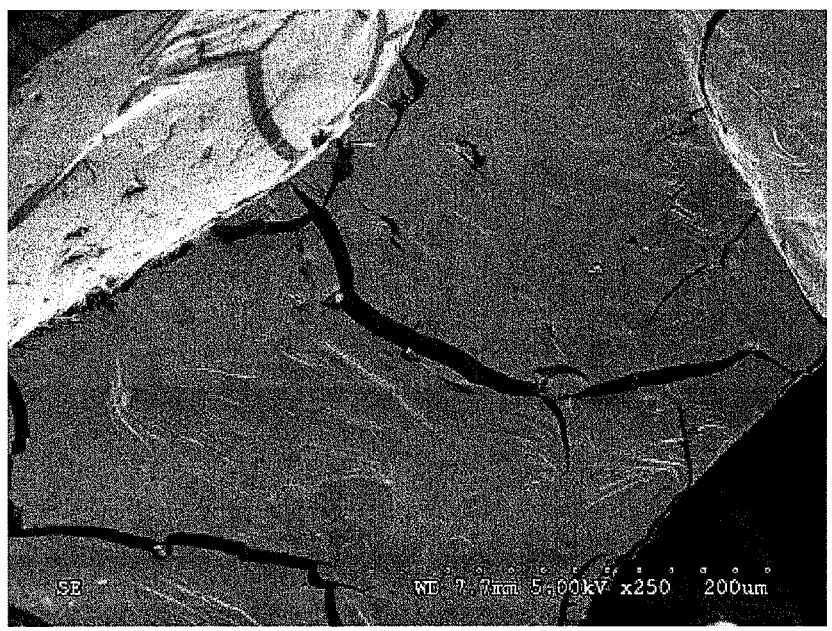
FIG. 9 shows a Scanning Electron Microscope (SEM) micrograph of static surface-treated "glass-like" carboxymethyl starch particles in accordance with an embodiment of the present disclosure.
Figure 10:
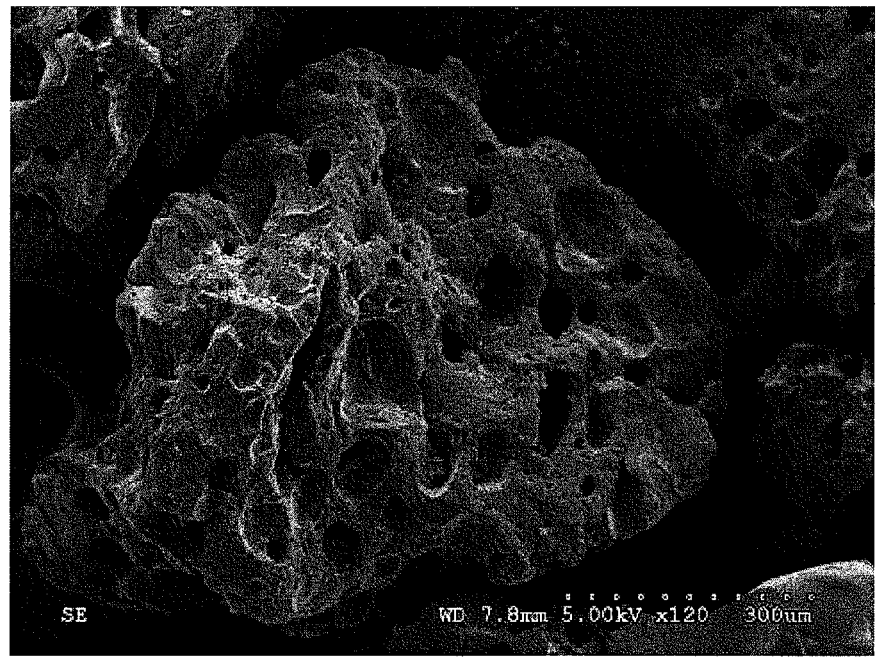
FIG. 10 shows a Scanning Electron Microscope (SEM) micrograph of non-surface treated porous carboxyalkylated polysaccharide particles in accordance with an embodiment of the present disclosure.
Figure 11:
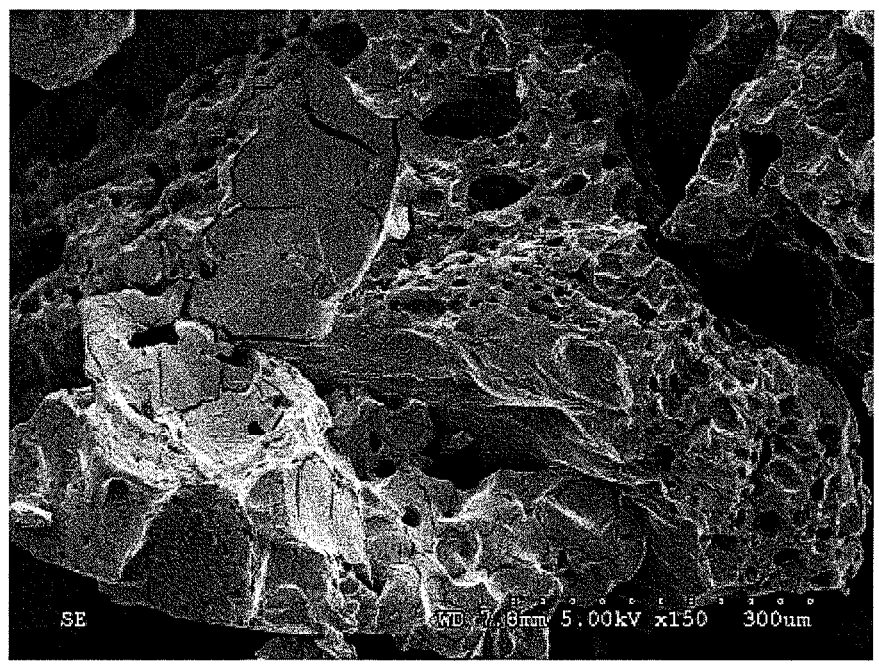
FIG. 11 shows a Scanning Electron Microscope (SEM) micrograph of surface-treated porous carboxyalkylated polysaccharide particles in accordance with an embodiment of the present disclosure.

| | Dynamic | Static |
| --- | --- | --- |
| FSC | 32 g/g | 32 g/g |
| CRC | 22 g/g | 20 g/g |
| AUL (0.7 psi) | 9.0 g/g | 15 g/g |
| SEM Figure | FIG. 8 | FIG. 9 |

Impact of Heating Time on Surface-Treated Carboxymethyl Starch

Figure 12:
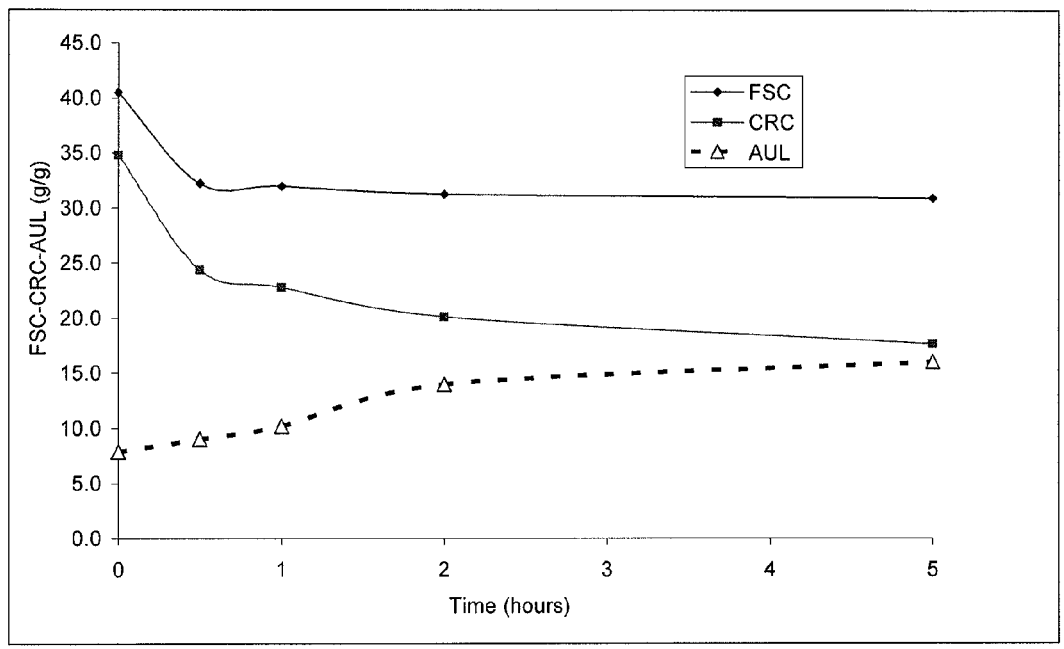
FIG. 12 shows a graph illustrating the FSC, CRC and AUL performance of a surface-treated carboxymethyl starch heated in a static environment (convection oven, programmed at 140° C.) over a period of 5 hours in accordance with an embodiment of the present disclosure.

The sieved product (5.0 g) from the preceding example was mixed with a citric acid solution (2.3 ml; 2.58 g of citric acid in 12 ml of water and 105 ml of isopropanol). The resulting slurry was placed on a watch glass and transferred into a convection oven where it was heated at 100° C. over a period of 10 minutes. The product was subsequently heated at 140° C. The absorbent characteristics of the resulting product (following a cooling period) were measured following a heating period at 140° C. of 0.5, 1, 2 and 5 hours (FIG. 12).

Impact of Heating Time on Surface-Treated Carboxymethyl Cellulose in a Convection Oven Carboxymethyl cellulose (Aqualon B315, 8% moisture content) was fed into the extruder at a rate of 3.8 kg/hr. An alkaline solution (pH 8.8) was subsequently injected at a rate of 37.6 kg/h. The extruder had the following barrel temperature profile: $Tb_1$=27° C. $Tb_2$=27° C., $Tb_3$=27° C., $Tb_4$=25° C., $Tb_5$=28° C., $Tb_6$=27° C., $Tb_7$=28 ° C., $Tb_8$=30° C. and $Tb_9$=24° C. The hydrogel product was produced at a rate of 38 kg/hr and a moisture content of 91%. The hydrogel was subsequently dried in a convection oven at 65° C., ground and sieved. The fraction between 20-100 Mesh (850 µm to 150 µm) was retained.

Figure 13:
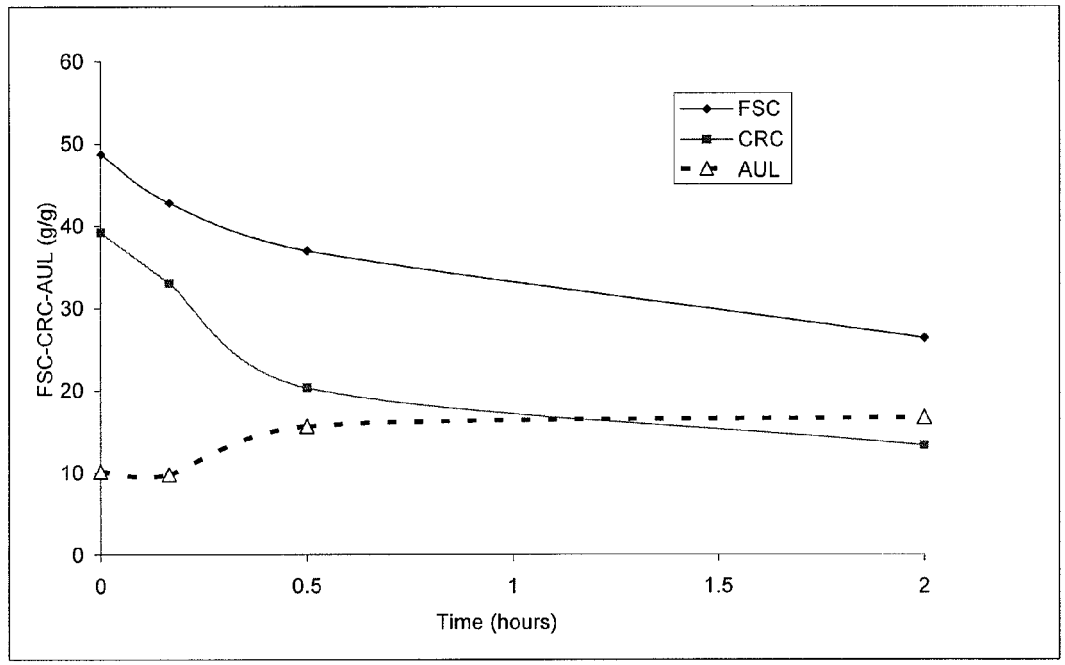
FIG. 13 shows a graph illustrating the FSC, CRC and AUL performance of a surface-treated carboxymethyl cellulose heated in a static environment (convection oven, programmed at 140° C.) over a period of 2 hours in accordance with an embodiment of the present disclosure.

The sieved product (5.0 g) was mixed with a citric acid solution (2.3 ml; 2.58 g of citric acid in 12 ml of water and 105 ml of isopropanol). The resulting slurry was placed on a watch glass and transferred into a convection oven where it was heated at 100° C. for 10 minutes. The product was subsequently heated at 140° C. The absorbent characteristics of the resulting product (following a cooling period) were measured following a heating period at 140° C. of 10, 30, and 120 minutes (FIG. 13).

Infra-Red Heat Treatment of CMS

Water (870 ml), wheat starch (330 g) and sodium hydroxide (5.5 g; 50% solution) were added to a two-liter beaker. The mixture was stirred over a period of 35 minutes at a temperature of 40° C. Epichlorohydrin (1.197 g) was subsequently added and the mixture allowed to react for an additional 35 minutes while stirring to produce a cross-linked starch slurry. Additional sodium hydroxide (147 g; 50% solution) was added and the slurry stirred for 5 minutes producing a gelatinized starch. The gelatinized starch was heated at 60° C. and mixed with sodium monochloroacetate (213 g; added stepwise over a period of 15 minutes). The gel was left to react for a period of 1 hour, precipitated by the addition of methanol (~7.0 liters) and filtered. The resulting precipitate was slurried in a methanol/water solution (2.0 liters; 9:1 V/V), the pH adjusted to 8.5-9.0 using hydrochloric acid and heated. The slurry was filtered, the residue re-slurried in a methanol/water solution (2.0 liters; 9:1 V/V) and filtered. An aliquot (1 ml) of the filtrate was taken and mixed with a few drops of silver nitrate. The absence of a silver chloride precipitate is indicative of product purity. Where a silver chloride precipitate was observed, the product was re-slurried again using a methanol/water solution (2.0 liters; 9:1 V/V) and filtered. This process was repeated until no further sliver chloride precipitation could be observed. The residue was subsequently purified by washing with methanol (2.0 liters), filtered and dried in a convection oven at 65° C.

Figure 14:
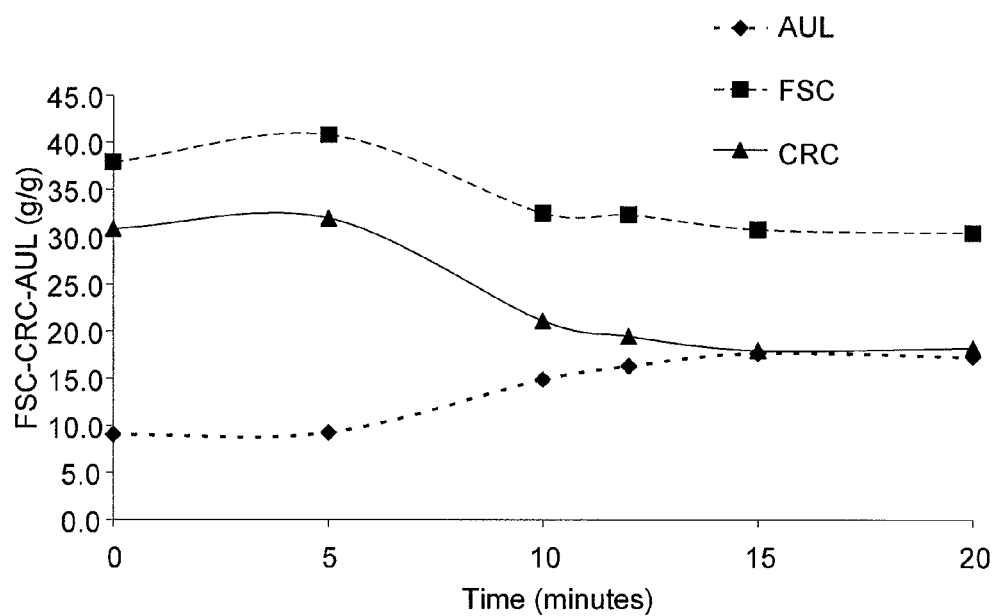
FIG. 14 shows a graph illustrating the FSC, CRC and AUL performance of a surface-treated carboxymethyl starch heated in a static environment (IR oven, programmed at 140° C.) over a period of 20 minutes in accordance with an embodiment of the present disclosure.
Figure 15:
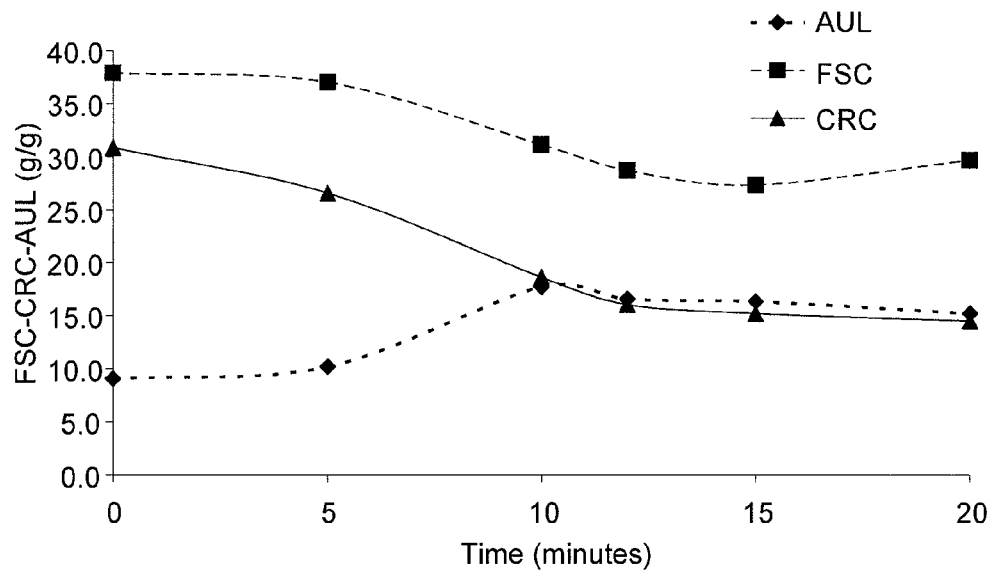
FIG. 15 shows a graph illustrating the FSC, CRC and AUL performance of a surface-treated carboxymethyl starch heated in a static environment (IR oven, programmed at 160° C.) over a period of 20 minutes in accordance with an embodiment of the present disclosure.
Figure 16:
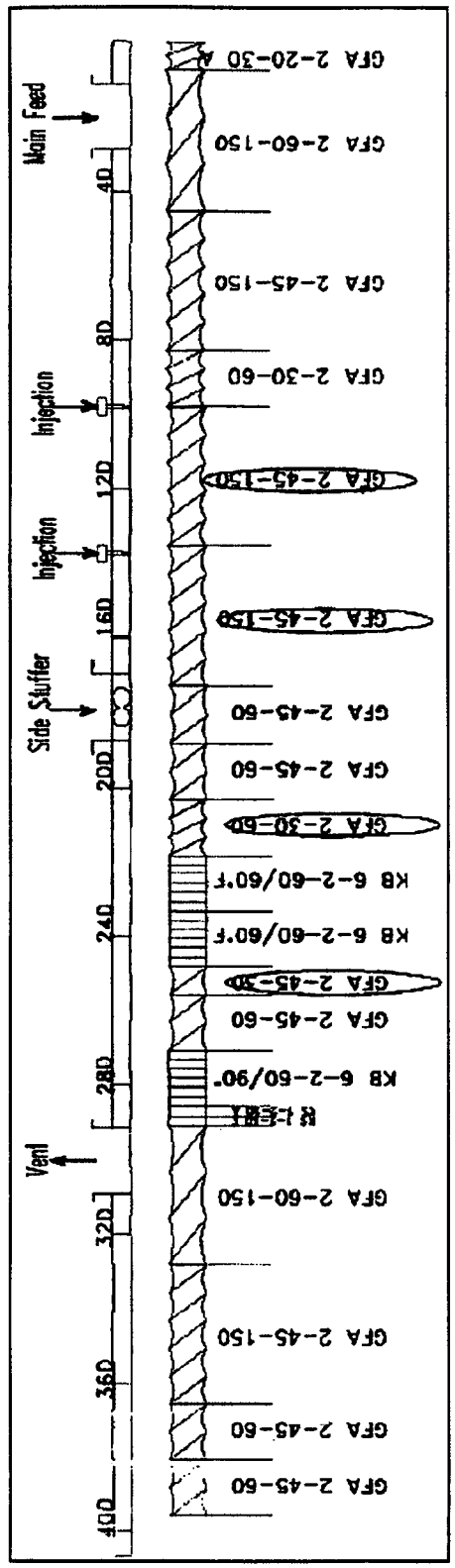
FIG. 16 is a side elevational view of an extruder screw in accordance with an embodiment of the present disclosure.

The dried product (100 g) was dispersed in water (900 ml) to form a hydrogel. The pH of the hydrogel was adjusted to 8.5-9.0. The hydrogel was subsequently dried in a convection oven at 65° C. The dried product was ground and sieved (20 and 100 Mesh). The sieved product (40 g) was mixed with a citric acid solution (18.0 ml; 5.16 g of citric acid in 24 ml of water and 210 ml of isopropanol). The slurry was evenly spread on a Pyrex™ pie dish and subsequently heated in a convection oven at 100° C. over a period of 18 minutes. The process was repeated with a further batch of dried product (40 g). The two samples were subsequently placed in an IR oven and heated at 140° C. and 160° C. respectively. The sample temperatures, as measured with an IR thermometer were however different from the programmed oven temperatures (Table 7). The absorbent characteristics of the samples (following a cooling period) were measured following a heating period of 5, 10, 12, 15, and 20 minutes (FIGS. 14 and 15).

TABLE 7

Programmed and Measured Temperatures

| Programmed Temperature | Time programmed | Measured temperature at various times | | | | |
|---|---|---|---|---|---|---|
| | | 2 min | 5 min | 10 min | 15 min | 20 min |
| 140° C. | 5 minutes | 121° C. | 141° C. | — | — | — |
| | 10 minutes | 118° C. | 161° C. | 160° C. | — | — |
| | 15 minutes | 123° C. | 166° C. | 159° C. | 162° C. | — |
| | 20 minutes | 120° C. | 141° C. | 156° C. | 168° C. | 167° C. |
| 160° C. | 5 minutes | 132° C. | 161° C. | — | — | — |
| | 10 minutes | 123° C. | 177° C. | 186° C. | — | — |
| | 15 minutes | 117° C. | 160° C. | 187° C. | 190° C. | — |
| | 20 minutes | 124° C. | 157° C. | 184° C. | 194° C. | 196° C. |

Starting temperature: 21° C.

Agglomerator Surface-Treated CMS

Water (900 ml), wheat starch (338 g; 14% moisture content) and sodium hydroxide (5.5 g; 50% solution) were added to a two-liter beaker. The mixture was stirred over a period of 35 minutes at a temperature of 40° C. Epichlorohydrin (1.20 g) was subsequently added and the mixture allowed to react for an additional 35 minutes while stirring to produce a cross-linked starch slurry. Additional sodium hydroxide (147 g; 50% solution) was added and the slurry stirred for 5 minutes producing a gelatinized starch. The gelatinized starch was heated at 60° C. and mixed with sodium monochloroacetate (214 g; added stepwise over a period of 15 minutes). The gel was left to react for a period of 1 hour, precipitated by the addition of methanol (~7.0 liters) and filtered. The resulting precipitate was slurried in a methanol/water solution (2.0 liters; 9:1 V/V), the pH adjusted to 8.5-9.0 using hydrochloric acid and heated. The slurry was filtered, the residue re-slurried in a methanol/water solution (2.0 liters; 9:1 V/V) and filtered. An aliquot (1 ml) of the filtrate was taken and mixed with a few drops of silver nitrate. The absence of a silver chloride precipitate is indicative of product purity. Where a silver chloride precipitate was observed, the product was re-slurried again using a methanol/water solution (2.0 liters; 9:1 V/V) and filtered. This process was repeated until no further sliver chloride precipitation could be observed. The residue was subsequently purified by washing with methanol (2.0 liters), filtered and dried in a convection oven at 65° C.

The dried product (300 g) was dispersed in water (2.7 liters) to form a hydrogel. The pH of the hydrogel was adjusted to 8.5-9.0. The hydrogel was subsequently dried in a convection oven at 65° C. The dried product was ground and sieved (20 and 100 Mesh).

The agglomerator parameters were adjusted as follows: air flow: 20 l/minute; air flow pressure: 15 psig (103 kPa); and air temperature: 70° C. About 50 g of the dried product was placed in the agglomerator. About 5.0 g of a citric acid solution (9.8 g of citric acid in 100 ml of water) was injected through a nozzle over a period of about 2 minutes. CMS particles having a moisture content of 10% were obtained. The particles were placed on a Pyrex™ pie dish and placed in an IR oven heated at a programmed temperature of 140° C. over a period of 12 minutes (the measured temperature after 12 minutes was about 160° C.). The product was allowed to cool and the absorbent characteristics measured (Table 8).

TABLE 8

| Agglomerator treated CMS characteristics | |
|---|---|
| FSC | 29 g/g |
| CRC | 16 g/g |
| AUL (0.7 psi) | 17 g/g |

TABLE 8-continued

Agglomerator treated CMS characteristics

| Physical appearance of swollen gel | Discrete gel particles |
|---|---|

Citric Acid Surface-Treated Carboxymethyl Wheat Starch

Water (900 ml), wheat starch (337 g; 12% moisture content) and sodium hydroxide (5.5 g; 50% solution) were added to a two-liter beaker. The mixture was stirred over a period of 35 minutes at a temperature of 40° C. Epichlorohydrin (1.204 g) was subsequently added and the mixture allowed to react for an additional 35 minutes while stirring to produce a cross-linked starch slurry. Additional sodium hydroxide (192 g; 50% solution) was added and the slurry stirred for 5 minutes producing a gelatinized starch. The gelatinized starch was heated at 60° C. and mixed with sodium monochloroacetate (213 g; added stepwise over a period of 15 minutes). The gel was left to react for a period of 1 hour, precipitated by the addition of methanol (~7.0 liters) and filtered. The resulting precipitate was slurried in a methanol/water solution (2.0 liters; 9:1 V/V), the pH adjusted to 8.5-9.0 using hydrochloric acid and heated. The slurry was filtered, the residue re-slurried in a methanol/water solution (2.0 liters; 9:1 V/V) and filtered. An aliquot (1 ml) of the filtrate was taken and mixed with a few drops of silver nitrate. The absence of a silver chloride precipitate is indicative of product purity. Where a silver chloride precipitate was observed, the product was re-slurried again using a methanol/water solution (2.0 liters; 9:1 V/V) and filtered. This process was repeated until no further sliver chloride precipitation could be observed. The residue was subsequently purified by washing with methanol (2.0 liters), filtered and dried in a convection oven at 65° C.

The dried product (300 g) was dispersed in water (2.7 liters) to form a hydrogel. The pH of the hydrogel was adjusted to 8.5-9.0. The hydrogel was subsequently dried in a convection oven at 65° C. The dried product was ground and sieved (20 and 100 Mesh). The sieved product (40 g) was mixed with a citric acid solution (18.0 ml; 2.58 g of citric acid in 12 ml of water and 105 ml of isopropanol). The slurry was evenly spread on a Pyrex™ pie dish (about 23 cm in diameter) having an even depth of about 1 mm. This cake was subsequently heated in convection mode at 100° C. over a period of 19 minutes. Further heating was accomplished in an IR oven at 140° C. over a period of 15 minutes. The absorbent characteristics of the resulting product were subsequently measured and are summarized hereinbelow in Table 9.

TABLE 9

Absorbent characteristics of citric acid surface-treated CMS (wheat)

| FSC | 29.7 g/g |
|---|---|
| CRC | 18.7 g/g |
| AUL (0.7 psi) | 16.2 g/g |

Manufacture of Carboxyalkylated Starches by Reactive Extrusion

Wheat starch having a moisture content of 11% was fed into a TSE (ZSE 40 mm) using an agitated gravimetric feeder, at a throughput of 9.25 kg/hr (20.4 lbs/hr). Sodium monochloroacetate was concomitantly fed into the extruder (gravimetric feeder) at a throughput of 4.2 kg/hr (9.3 lbs/hr). A sodium hydroxide solution (36%) was injected at a throughput of 4.03 kg/hr (8.9 lbs/hr). The water content of the wheat starch was increased to about 20.6%. The extruder had the following barrel temperature profile: $Tb_2=29°$ C. $Tb_3=29°$ C., $Tb_4=32°$ C., $Tb_5=43°$ C., $Tb_6=65°$ C., $Tb_7=121°$ C., $Tb_8=101°$ C., $Tb_9=87°$ C. and $Tb_{10}=85°$ C. The screw speed was set at 200 rpm and the screw load at 34%. The TSE was equipped with a die comprising 10 holes (3 mm in diameter). The die discharge pressure was 144 kPa (21 Psig). The extrudate had a temperature of 102° C. The extrudate was subsequently oven dried to a moisture content of 6.7%, ground and sieved (16 and 50 Mesh being the fraction retained). The DS was characterized according to method ASTM D1439-83a. A reaction efficiency of 80% was obtained.

The dried product (85 g) was dispersed in a methanol/water solution (500 ml; 85:15 V/V) at 60° C. for 90 minutes. The conductance was measured to be 8300 µS/cm; the pH was recorded to be 8.5. The product was filtered and dispersed in a methanol/water solution (500 ml; 85:15 V/V) at 60° C. for 90 minutes. The conductance was measured to be 3030 µS/cm; the pH was recorded to be 8.4. The product was filtered and dispersed in a methanol/water solution (500 ml; 85:15 V/V) at 60° C. for 90 minutes. The conductance was measured to be 2250 µS/cm; the pH was recorded to be 8.5. The product was filtered and dispersed in a methanol/water solution (500 ml; 85:15 V/V) at 60° C. for 90 minutes. The conductance was measured to be 900 µS/cm; the pH was recorded to be 8.3. The product was filtered and dispersed in a methanol/water solution (500 ml; 85:15 V/V) at 60° C. for 90 minutes. The conductance was measured to be 670 µS/cm; the pH was recorded to be 8.5. The product was filtered and dispersed in a methanol/water solution (500 ml; 85:15 V/V) at 60° C. for 90 minutes. The conductance was measured to be 450 µS/cm; the pH was recorded to be 8.5. The product was filtered and dispersed in a methanol/water solution (500 ml; 85:15 V/V) at 60° C. for 90 minutes. The conductance was measured to be 485 µS/cm; the pH was recorded to be 8.5. The product was finally filtered and dried in a convection oven at 65° C.

The dried product (5.0 g) was mixed with a citric acid solution (2.3 ml; 2.58 g of citric acid in 12 ml of water and 105 ml of isopropanol). The slurry was evenly spread on a watch glass and heated in convection mode at 100° C. over a period of 10 minutes. Further heating was accomplished in an IR oven at 140° C. over a period of 12 minutes. The absorbent characteristics of the resulting product were subsequently measured and are summarized hereinbelow in Table 10.

TABLE 10

Absorbent characteristics of citric acid surface-treated CMS (wheat)

| FSC | 33 g/g |
|---|---|
| CRC | 20 g/g |
| AUL (0.7 psi) | 16 g/g |

In an embodiment of the present disclosure, starch was fed into the extruder at a throughput of 28.0 lbs/hr. Sodium monochloroacetate was concomitantly fed into the extruder at a throughput of 13.0 lbs/hr. Tap water was injected through a first nozzle positioned 400 mm downstream the extruder, at a rate of 4.8 lbs/hr. A sodium hydroxide solution (50%) was injected through the nozzle at a rate of 9.0 lbs/hr. The subsequent purification and surface-treatment was carried out according to the protocol as described hereinabove. The product was subsequently analyzed by SEM (FIGS. 8 and 9)

It is to be understood that the disclosure is not limited in its application to the details of construction and parts as described hereinabove. The disclosure is capable of other embodiments and of being practiced in various ways. It is also understood that the phraseology or terminology used herein is for the purpose of description and not limitation. Hence, although the present disclosure has been described hereinabove by way of illustrative embodiments thereof, it can be modified without departing from the spirit, scope and nature as defined in the appended claims.

What is claimed is:

1. A superabsorbent material comprising: a particle formed of a carboxyalkylated polysaccharide having a pH in a range from about 5.0 to about 10, said particle having an interior and a surface, each exhibiting a differentiated functionality; said interior is absorbent; said surface is treated with a non-crosslinking acid in the presence of an organic solvent, such that penetration depth of said non-crosslinking acid is limited to said surface, said non-crosslinking acid induces ester linkages between polysaccharide strands at said particle surface, which imparts said particle with a sufficient structural rigidity to enable said particle to maintain a discrete particle shape when contacted with a salt solution, and said superabsorbent material exhibits an absorption under load (AUL) at 0.7 psi of at least 14 g/g and a centrifuge retention capacity (CRC) of at least 18 g/g.

2. The superabsorbent material according to claim 1, wherein said carboxyalkylated polysaccharide particle exhibits a discrete gel particle shape when swollen to its maximum volume in saline solution.

3. The superabsorbent material according to claim 1, wherein said non-crosslinking agent includes HCl, acetic acid, glycolic acid, stearic acid, and other organic or inorganic monovalent acids.

4. The superabsorbent material according to claim 1, wherein said carboxyalkylated polysaccharide particle has a greater absorbance under load (AUL) of said salt solution at 0.7 psi than a comparative particle formed of the carboxyalkylated polysaccharide having a surface that is not treated with the non-crosslinking acid.

5. The superabsorbent material according to claim 1, wherein said carboxyalkylated polysaccharide particle exhibits at least one property selected from the group consisting of: an AUL at 0.7 psi of at least 14 g/g, a centrifuge retention capacity (CRC) of at least 18 g/g, and a free swell capacity (FSC) of at least 26 g/g.

6. The superabsorbent material according to claim 1, wherein said carboxyalkylated polysaccharide exhibits the presence of an ester shoulder or ester band as determined by ATR-IR spectroscopy.

7. The superabsorbent material according to claim 1, wherein said carboxyalkylated polysaccharide particle has a size in a range from about 150 μm to about 850 μm.

8. The superabsorbent material according to claim 1, wherein said carboxyalkylated polysaccharide has a degree of substitution ranging from 0.2 to 1.0.

9. The superabsorbent material according to claim 1, wherein said carboxyalkylated polysaccharide has a homogeneous carboxyalkyl distribution pattern.

10. The superabsorbent material according to claim 1, wherein said carboxyalkylated polysaccharide particle is glass-like.

11. The superabsorbent material according to claim 1, wherein said carboxyalkylated polysaccharide has a biobased content of at least 82%.

12. The superabsorbent material according to claim 1, wherein said carboxyalkylated polysaccharide is a carboxymethyl starch.

13. The superabsorbent material according to claim 1, wherein said carboxyalkylated polysaccharide is internally crosslinked with ionic or ether linkages.

14. The superabsorbent material according to claim 1, wherein said salt solution is a 0.9% solution of NaCl.

15. A hygiene article comprising an absorbent member, said absorbent member has a content between about 15% to about 80% of a carboxyalkylated polysaccharide particle according to claim 1, said hygiene article exhibiting at least one property selected from the group consisting of: a third acquisition rate of at least 0.22 ml/sec.; a third rewet of at most 4.0 grams; an averaged acquisition rate of at least 0.12 mi/sec., and a total rewet of at most 6.0 grams.

16. The hygiene article according to claim 15, wherein said absorbent member has carboxyalkylated polysaccharide particle content of between about 30% to about 60%.

17. The hygiene article according to claim 15, wherein said hygiene article is selected from the group consisting of diapers, incontinence articles, sanitary napkins, feminine hygiene products, and absorbent dressings.

* * * * *